(12) United States Patent
Vanasse et al.

(10) Patent No.: US 12,708,378 B2
(45) Date of Patent: Aug. 18, 2026

(54) ADJUSTABLE ANGLE SURGICAL REAMER DRIVER

(71) Applicant: Advita Ortho, LLC, Gainesville, FL (US)

(72) Inventors: Thomas M. Vanasse, Gainesville, FL (US); Adam Marrocco, Gainesville, FL (US); Ben Stewart, Gainesville, FL (US); C. Michael Mauldin, Lake City, FL (US)

(73) Assignee: Advita Ortho, LLC, Gainesville, FL (US)

( * ) Notice: Subject to any disclaimer, the term of this patent is extended or adjusted under 35 U.S.C. 154(b) by 0 days.

(21) Appl. No.: 18/827,281

(22) Filed: Sep. 6, 2024

(65) Prior Publication Data

US 2025/0082343 A1 Mar. 13, 2025

Related U.S. Application Data

(60) Provisional application No. 63/581,528, filed on Sep. 8, 2023.

(51) Int. Cl.
*A61B 17/16* (2006.01)
*A61B 17/17* (2006.01)
(Continued)

(52) U.S. Cl.
CPC .......... *A61B 17/1631* (2013.01); *A61B 17/17* (2013.01); *A61B 90/08* (2016.02);
(Continued)

(58) Field of Classification Search
CPC .................................................. A61B 17/1684
See application file for complete search history.

(56) References Cited

U.S. PATENT DOCUMENTS 8,475,460 B1 7/2013 Roger et al.
8,480,674 B1 * 7/2013 Roger ................ A61B 17/1666 606/91

(Continued)

OTHER PUBLICATIONS

International Search Report and Written Opinion from International Application No. PCT/US2024/045659 mailed Jan. 13, 2025.

*Primary Examiner* — Zade Coley
(74) *Attorney, Agent, or Firm* — GREENBERG TRAURIG, LLP

(57) ABSTRACT

A device including a housing having a passage extending therethrough defining a drive shaft axis; a drive shaft supported within the passage and rotatable about the drive shaft axis; a drive housing defining a reaming axis and pivotably coupled to the housing to allow the reaming axis to deflect with respect to the drive shaft axis, a drive interface supported within the drive housing and rotatable about the reaming axis, the drive interface contacting the drive shaft such that rotation of the drive shaft about the drive shaft axis causes rotation of the drive interface about the reaming axis; and an angle adjustment control positioned remotely from a distal end of the housing and operably coupled to the drive housing to move the drive housing between a first position and a second position to define respective first and second offset angles between the reaming axis and the drive shaft axis.

21 Claims, 18 Drawing Sheets

(51) Int. Cl.
*A61B 90/00* (2016.01)
*A61B 17/00* (2006.01)

(52) U.S. Cl.
CPC ............... *A61B 2017/00477* (2013.01); *A61B 2090/0811* (2016.02)

(56) References Cited

U.S. PATENT DOCUMENTS

| | | | | |
|---|---|---|---|---|
| 10,028,838 | B2 * | 7/2018 | Hodorek | A61F 2/4081 |
| 10,034,777 | B2 * | 7/2018 | Poncet | A61B 17/15 |
| 10,499,929 | B2 * | 12/2019 | Sohn | A61B 17/1778 |
| 12,558,109 | B2 * | 2/2026 | Fiedler | A61B 17/162 |
| 2004/0097947 | A1 * | 5/2004 | Wolford | A61B 17/1617 606/80 |
| 2005/0159751 | A1 | 7/2005 | Berthusen et al. | |
| 2017/0311959 | A1 | 11/2017 | Weekes et al. | |
| 2021/0015494 | A1 * | 1/2021 | Flatters | A61B 17/1666 |
| 2021/0100562 | A1 * | 4/2021 | Rodriguez | A61B 17/1662 |
| 2022/0192682 | A1 * | 6/2022 | Fiedler | A61B 17/1664 |
| 2023/0181199 | A1 * | 6/2023 | Orphanos | A61B 17/1659 606/80 |

* cited by examiner 300
304
320
310
306

300
304
310
302
306

302
300
304
308
306

100

100

750
761
760
628
612
744
730
734
630
614
652
600
650
654
656
670
672
620
660
690
680
720

636
750
761
760
616
628
620
742
740
632
730
734
610
652
600
650
654
656
618
660
634
690
680
720

ADJUSTABLE ANGLE SURGICAL REAMER DRIVER

CROSS-REFERENCE

This is a section 111(a) application relating to and claiming the benefit of commonly-owned, U.S. Provisional Patent Application No. 63/581,528, filed on Sep. 8, 2024 and entitled "ADJUSTABLE SURGICAL REAMER DRIVER," the contents of which are incorporated herein by reference in their entirety.

FIELD OF THE INVENTION

The field of invention relates to orthopedic surgery. More particularly, the field of invention relates to orthopedic surgical reaming tools that are operable to provide an adjustable offset angle between a reaming axis that defines a reamed surface and a drive axis along which a drive shaft is aligned.

BACKGROUND OF THE INVENTION

During orthopedic surgery, surgical reamers are used to remove tissue from bones of patients to prepare the bones to receive prosthetic implants. For example, during shoulder arthroplasty, a surgical reamer may be used to remove tissue from the contact surface of a patient's glenoid to prepare the glenoid to receive a glenoid implant. In some cases, the selected prosthetic implant may require the surgical reamer to be applied to the tissue along an axis that is not parallel to a drive axis of the surgical reamer, such as a neutral axis of the bone.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

SUMMARY

Figures 1A, 1B:
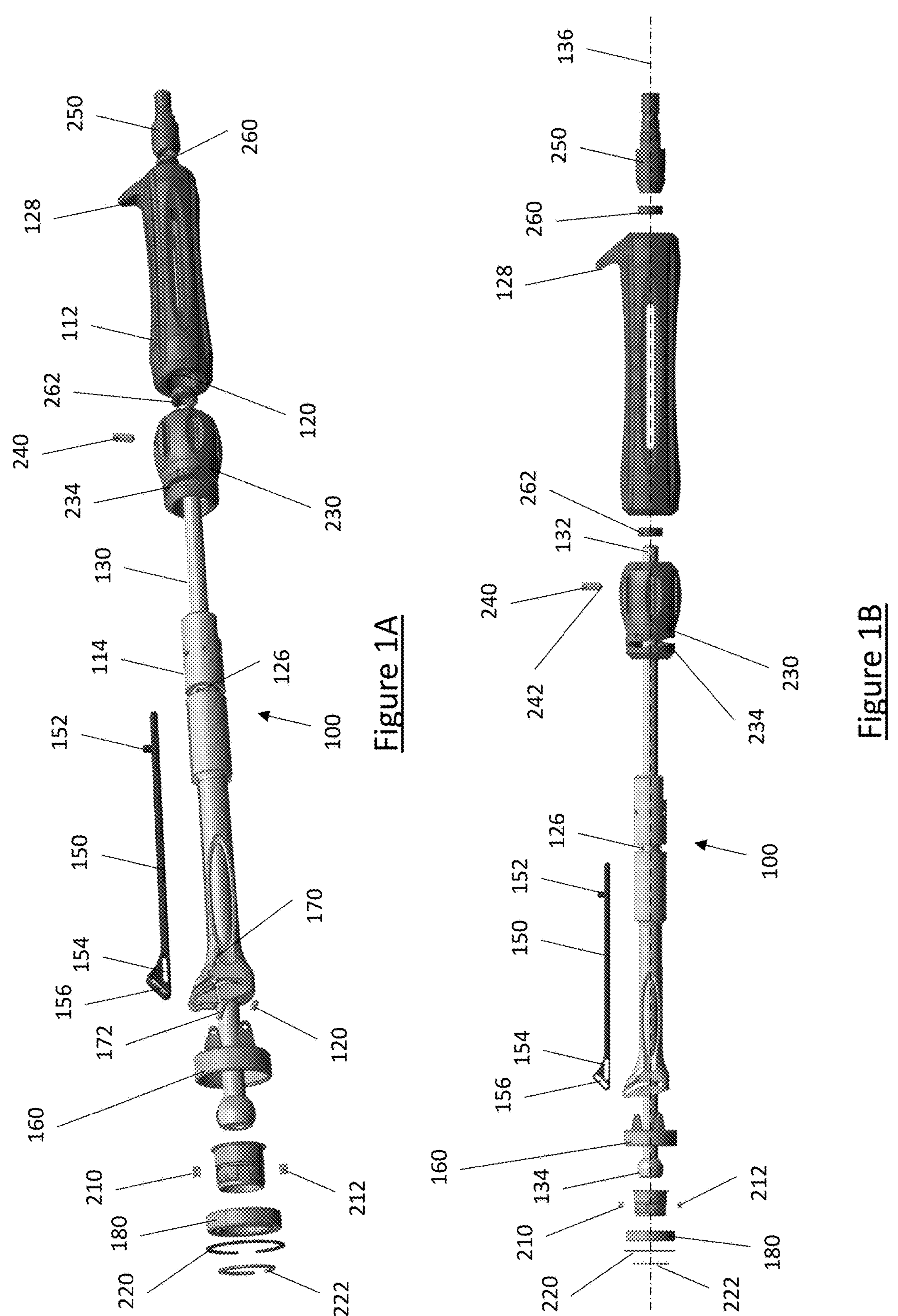
FIG. 1A shows an exploded perspective view of an exemplary reaming device.
FIG. 1B shows an exploded side view of the exemplary reaming device shown in FIG. 1A.

In some embodiments, a device for reaming a bone of a patient includes a housing configured to be gripped by a user, wherein the housing includes a proximal end and a distal end opposite the proximal end, wherein a passage extends through the housing from the proximal end to the distal end, wherein the passage defines a drive shaft axis; a drive shaft received within the passage, wherein the drive shaft includes a proximal end and a distal end, wherein the drive shaft is supported within the passage so as to be rotatable about the drive shaft axis with respect to the housing, wherein a cannula is formed in the distal end of the drive shaft, wherein the cannula is configured to receive a guide pin; a drive housing pivotably coupled to the housing, wherein the drive housing defines a reaming axis, wherein the drive housing is pivotable with respect to the housing so as to cause the reaming axis to deflect with respect to the drive shaft axis, a drive interface element positioned within the drive housing, wherein the drive interface element is supported within the drive housing such that the drive interface element is allowed to rotate about the reaming axis with respect to the drive housing, wherein the drive interface element contacts the distal end of the drive shaft such that rotation of the drive shaft about the drive shaft axis causes rotation of the drive interface element about the reaming axis, wherein the drive interface element is configured to removably receive a reaming head, wherein, when the reaming head is removably received by the drive interface element, rotation of the drive interface element about the reaming axis causes rotation of the reaming head about the reaming axis; and an angle adjustment control element positioned remotely from the distal end of the housing, wherein the angle adjustment control element is operably coupled to the drive housing, wherein the angle adjustment control element is operable to move the drive housing between at least: a first position, wherein the drive housing defines a first offset angle between the reaming axis and the drive shaft axis, and a second position, wherein the drive housing defines a second offset angle between the reaming axis and the drive shaft axis, wherein the second offset angle is greater than the first offset angle.

In some embodiments, the distal end of the drive shaft includes at least one torque transmitting surface, the drive interface element includes at least one torque receiving surface, and the drive interface element is positioned within the drive housing such that the at least one torque transmitting surface of the drive shaft and the at least one torque receiving surface of the drive interface element abut one another.

In some embodiments, the device also includes a linkage coupling the angle adjustment control element to the drive housing. In some embodiments, the linkage has a proximal end and a distal end opposite the proximal end of the linkage, the angle adjustment control element is positioned on the housing so as to be pivotable with respect to the housing about the drive shaft axis, the linkage is positioned on the housing so as to be movable with respect to the housing along the drive shaft axis, the angle adjustment control element engages the proximal end of the linkage such that pivoting movement of the angle adjustment control element about the drive shaft axis causes linear movement of the linkage along the drive shaft axis, and the distal end of the linkage engages the drive housing such that linear movement of the linkage along the drive shaft axis causes the drive housing to pivot so as to adjust the offset angle. In some embodiments, the linkage is color-contrasting so as to identify a proper orientation of the device about a guide pin.

In some embodiments, the housing includes a fin, wherein the fin extends from the proximal end of the housing, and wherein the fin is positioned so as to identify a proper orientation of the device about a guide pin.

In some embodiments, the device also includes a reaming head removably engaged to the drive interface element. In some embodiments, the drive interface element includes a plurality of torque transmitting surfaces, the reaming head includes a plurality of torque receiving surfaces, and each of the plurality of torque transmitting surfaces of the drive interface element abuts a corresponding one of the plurality of torque receiving surfaces of the reaming head when the reaming head is removably engaged to the drive interface element, whereby the drive interface element drives rotation of the reaming head about the reaming axis when the drive interface element is rotated about the reaming axis. In some embodiments, the reaming head includes a central bore, and the central bore is sized to allow the guide pin to pass through the central bore and into the cannula of the drive shaft.

In some embodiments, the angle adjustment control element is configured to allow a user to adjust the offset angle without the user contacting a distal end of the device.

In some embodiments, the angle adjustment control element includes an adjustment knob. In some embodiments, the adjustment knob is positioned on the housing between the proximal end of the housing and the distal end of the housing.

In some embodiments, a kit includes the device; a reaming head configured to removably engage the drive interface element of the device; a first glenoid component of a shoulder prosthesis, wherein the first glenoid component includes a first augment angle, and wherein the first augment angle corresponds to the first offset angle between the reaming axis and the drive axis; and a second glenoid component of a shoulder prosthesis, wherein the second glenoid component includes a second augment angle, and wherein the second augment angle corresponds to the second offset angle between the reaming axis and the drive axis.

In some embodiments, a method includes positioning one of a guide pin or a guide hole along a neutral axis of a glenoid of a of a patient; providing a surgical reamer driver, wherein the surgical reamer driver has a drive shaft axis and a reaming axis, wherein the surgical reamer driver is configurable to provide at least a first offset angle or a second offset angle between the drive shaft axis and the reaming axis, wherein the surgical reamer driver has a cannulated drive shaft; configuring the surgical reamer driver to provide a selected one of the first offset angle or the second offset angle; coupling a reaming head to the surgical reamer driver; advancing the cannulated drive shaft of the surgical reamer driver along the one of the guide pin or the guide hole; and operating the surgical reamer driver to ream bone of the glenoid.

In some embodiments, the method also includes prior to operating the surgical reamer driver to ream the bone of the glenoid, aligning the surgical reamer driver about the guide pin with reference to a defect in the glenoid. In some embodiments, the aligning is performed by aligning a visual indicator of the surgical reamer driver with the defect. In some embodiments, the visual indicator includes at least one of a protrusion from the surgical reamer driver or a color-contrasting element of the surgical reamer driver.

In some embodiments, the method also includes selecting a selected glenoid component of a shoulder prosthesis from a set of glenoid components. In some embodiments, the selected glenoid component includes a selected augment angle, and the selected augment angle corresponds to the selected one of the first offset angle or the second offset angle. In some embodiments, the method also includes after operating the surgical reamer drive to ream the bone of the glenoid, implanting the selected glenoid component on the glenoid.

In some embodiments, the positioning one of the guide pin or the guide hole along a neutral axis of a glenoid of a of a patient includes forming the guide hole in the glenoid, and the advancing the cannulated drive shaft of the surgical reamer driver along the guide hole includes: placing a pilot tip in the cannulated drive shaft, and advancing the pilot tip into the guide hole.

DETAILED DESCRIPTION OF THE DRAWINGS

The exemplary embodiments relate to surgical reamers. More particularly, the exemplary embodiments relate to surgical reamers that provide an offset between a drive axis (e.g., a neutral axis of a patient's anatomy) and a reaming axis about which a reaming head rotates, and, in particular, to surgical reamers that allow such an offset to be adjusted.

Figure 1C:
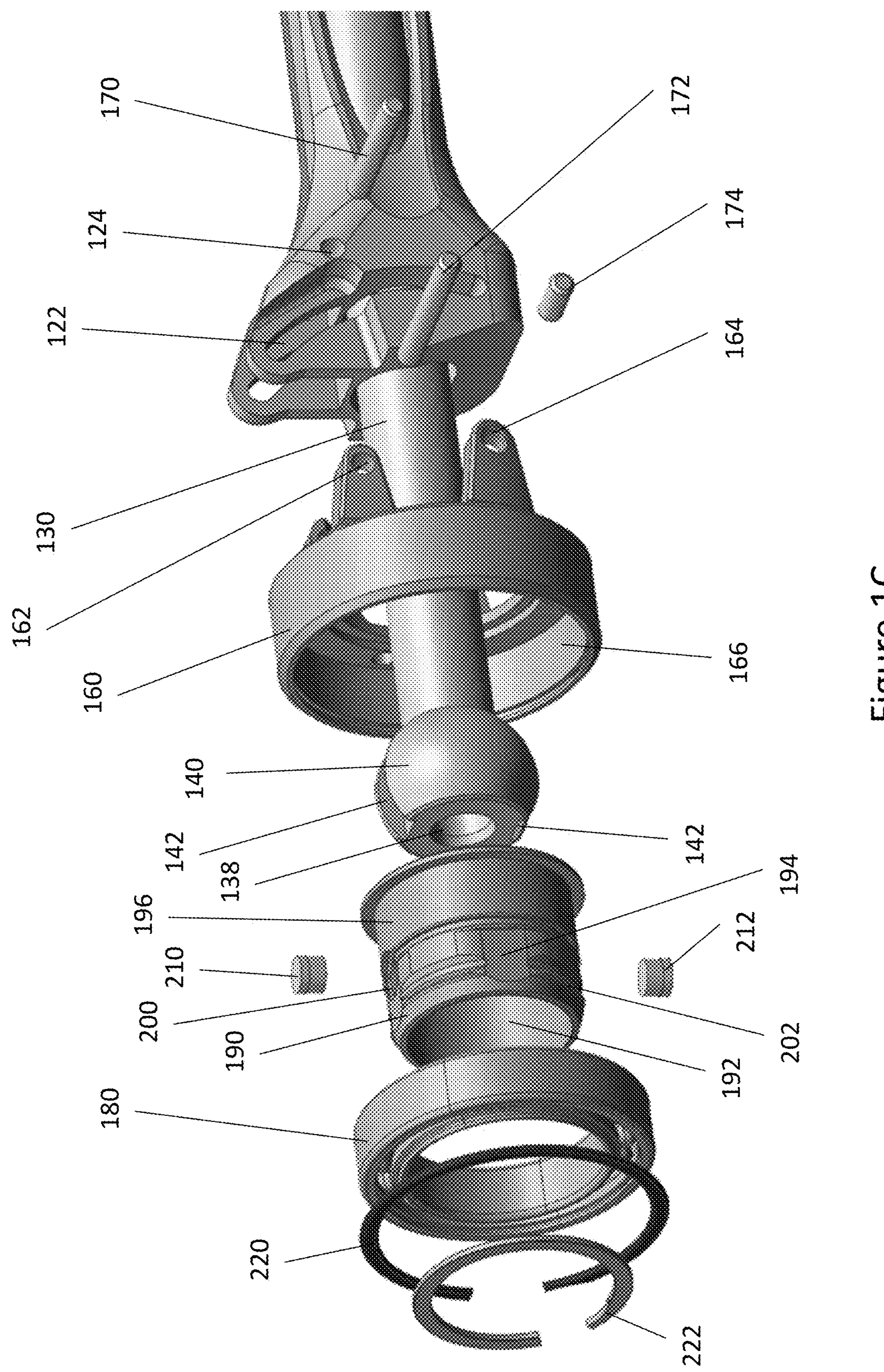
FIG. 1C shows an exploded perspective view of the distal end of the exemplary reaming device shown in FIG. 1A.

FIGS. 1A-1C illustrate an exemplary reaming device 100 according to some embodiments disclosed herein. In some embodiments, the reaming device 100 is configured to prepare, or remove, bone from the glenoid of the subject to thereby facilitate subsequent implantation of a glenoid component of a shoulder prosthesis. The exemplary reaming device 100 is described herein specifically with reference to a glenoid, but in other embodiments, exemplary reaming devices may be configured to treat other bones. The reaming device 100 includes a proximal end 102 and a distal end 104 opposite the proximal end 102 (see FIG. 3A).

In some embodiments, the reaming device 100 includes a housing 110 (see FIG. 3A) that is formed from a handle 112 and a drive shaft sleeve 114, and which is configured to be gripped by a user. In some embodiments, the housing 110 is a unitary or monoblock element (e.g., the housing 110 includes the handle 112 and the drive shaft sleeve 114 that are formed from a single piece of material). In some embodiments, the housing 110 includes one or more pieces joined together to one another (e.g., the handle 112 and the drive shaft sleeve are formed separately and are joined to one another, such as by welding or thermal assembly). In some embodiments, the housing 110 (e.g., the handle 112 thereof) is configured to be held by a user (e.g., a surgeon) in order to operate the reaming device 100 so as to ream bone as described herein. The housing 110 includes a proximal end 116 that is positioned proximate to the proximal end 102 of the reaming device 100, and includes a distal end 118 that is positioned proximate to the distal end 104 of the reaming device 100. In some embodiments, a channel 120 (e.g., a passage) is defined within the housing 110 (e.g., extends through both the handle 112 and the drive shaft sleeve 114). In some embodiments, a curved slot 122 and a transverse hole 124 extend through the drive shaft sleeve 114 near the distal end 118 of the housing 110. In some embodiments, the location and shape of the curved slot 122 and of the transverse hole 124 define adjustment of the reaming device 100 as will be described hereinafter. In some embodiments, the drive shaft sleeve 114 includes a hole array 126 arrayed about the drive shaft sleeve 114 and defining adjustment of the reaming device 100 as will be described hereinafter. In some embodiments, the housing 110 includes a fin 128 that is positioned diametrically opposed to the adjustment direction of the reaming device 100 (see, for example, FIGS. 4G and 4H), as will be described in further detail hereinafter.

In some embodiments, the reaming device 100 includes a drive shaft 130. In some embodiments, the drive shaft 130 is received within the channel 120 of the housing 110. In some embodiments, the drive shaft 130 includes a proximal end 132 that is positioned proximate to the proximal end 102 of the reaming device 100, and includes a distal end 134 that is positioned proximate to the distal end 104 of the reaming device 100. In some embodiments, a drive axis 136 is defined along the drive shaft 130 between the proximal end 132 and the distal end 134. In some embodiments, the drive shaft 130 is rotatably received within the channel 120 of the housing 110 such that the drive shaft 130 can rotate and be driven about the drive axis 136, and cannot move along the drive axis 136. In some embodiments, a cannula 138 extends through the drive shaft 130 from the proximal end 132 to the distal end 134. In some embodiments, the drive shaft 130 having a cannula 138 is referred to as a "cannulated drive shaft". In some embodiments, the cannula 138 is configured to receive a guide pin, such as a Kirschner wire (i.e., a "K-wire"). In some embodiments, the distal end 134 of the drive shaft 130 has a rounded head 140. In some embodiments, drive slots 142 are formed within the rounded head 140.

In some embodiments, the reaming device 100 includes a linkage 150 that is positioned adjacent to and extends generally along the drive shaft sleeve 114. In some embodiments, the linkage 150 includes an adjustment pin 152, an axial slot 154, and an angled slot 156, which cooperate to allow the linkage 150 to adjust the operation of the reaming device 100 by motion of the linkage 150 in a direction parallel to the drive axis 136 as will be described hereinafter.

In some embodiments, the reaming device 100 includes a drive square housing 160 (e.g., a drive housing) that is positioned at the distal end 118 of the housing 110. In some embodiments, the drive square housing 160 is pivotably coupled to the distal end 118 of the housing 110 such that the drive square housing 160 is able to pivot about a pivot axis that is perpendicular to the drive axis 136 of the drive shaft 130. In some embodiments, the drive square housing 160 includes a first transverse hole 162 and a second transverse hole 164, which together allow the orientation of the drive square housing 160 to be adjusted as will be described hereinafter. In some embodiments, the drive square housing 160 includes a bore 166 that is sized and shaped to retain and position a bearing as will be described hereinafter. In some embodiments, the orientation of the bore 166 within the drive square housing 160 defines a reaming axis 168.

In some embodiments, the reaming device 100 includes a first dowel pin 170. In some embodiments, the first dowel pin 170 is fixedly positioned (e.g., welded) within the transverse hole 124 of the drive shaft sleeve 114. In some embodiments, the first dowel pin 170 is also positioned within the axial slot 154 of the linkage 150 such that the linkage 150 can move longitudinally (e.g., along the drive axis 136) with respect to the first dowel pin 170 and the drive shaft sleeve 114, with the longitudinal movement of the linkage 150 constrained by the size of the axial slot 154 and the location of the first dowel pin 170.

In some embodiments, the reaming device 100 includes a second dowel pin 172. In some embodiments, the second dowel pin 172 is fixedly positioned (e.g., welded) within the first transverse hole 162 of the drive square housing 160. In some embodiments, the second dowel pin 172 also extends through, and is slidably positioned within, the angled slot 156 of the linkage 150 and the curved slot 122 of the of the drive shaft sleeve 114. In some embodiments, the positioning of the second dowel pin 172 within the first transverse hole 162, the angled slot 156, and the curved slot 122 allows motion of the linkage 150 in a direction parallel to the drive axis 136 to adjust the orientation of the drive square housing 160 as will be described hereinafter.

In some embodiments, the reaming device 100 includes third and fourth dowel pins 174. In some embodiments, the third and fourth dowel pins 174 (only one of which is visible in the figures) are fixedly positioned within (e.g., welded within) opposite sides the second transverse hole 164 of the drive square housing 160, such that the third dowel pin 174 is positioned to a first side of the drive shaft 130 and the fourth dowel pin 174 is positioned to an opposite second side of the drive shaft 130. In some embodiments, the third dowel pin 174 and the fourth dowel pin 174 are also slidably positioned within the curved slot 122 of the drive shaft sleeve 114 such that the third dowel pin 174 and the fourth dowel pin 174 slide within the curved slot 122 as the drive square housing 160 is adjusted, thereby contributing to definition of adjustment of the drive square housing 160 as will be described hereinafter.

In some embodiments, the reaming device 100 includes a bearing 180 positioned within the bore 166 of the drive square housing 160. In some embodiments, such as shown in FIGS. 1A-1C, the bearing 180 is a ball bearing. In some embodiments, the bearing 180 is a radial ball bearing of the type commercialized by SPB-USA of Sarasota, Florida under part number ER1212. In some embodiments, the bearing is a plain bearing, such as a bushing. In some embodiments, the bearing 180 is positioned within the bore 166 of the drive square housing 160 such that, when the orientation of the drive square housing 160 is adjusted as will be described hereinafter to thereby adjust the orientation of the reaming axis 168, the orientation of the bearing 180 is adjusted correspondingly.

Figure 4A:
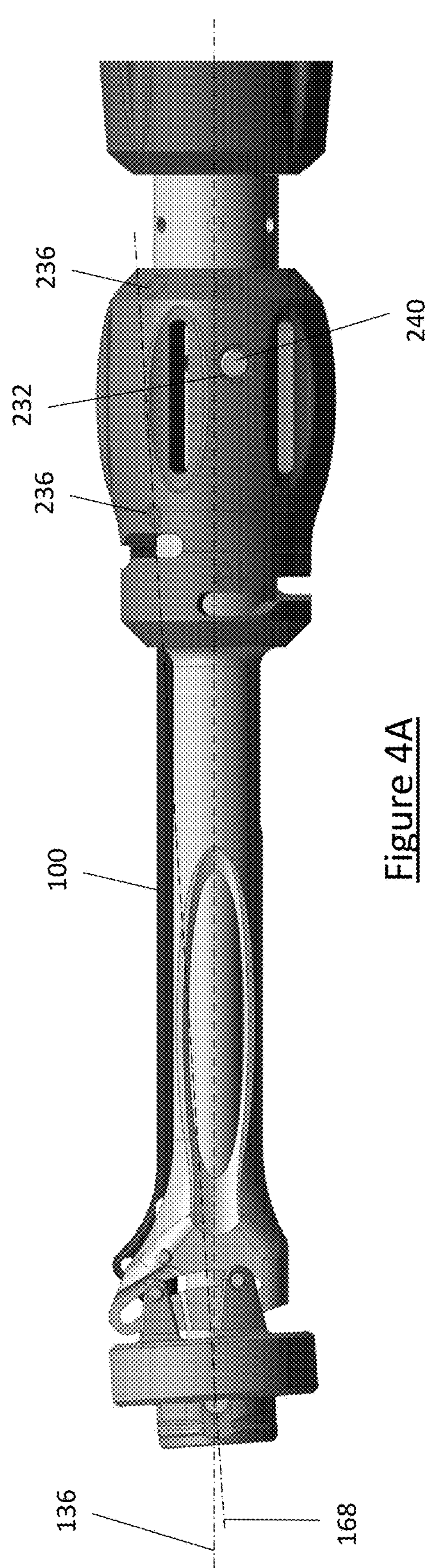
FIG. 4A shows a partial side view of the exemplary reaming device shown in FIGS. 1A and 1B as configured to provide a first offset.
Figure 4B:
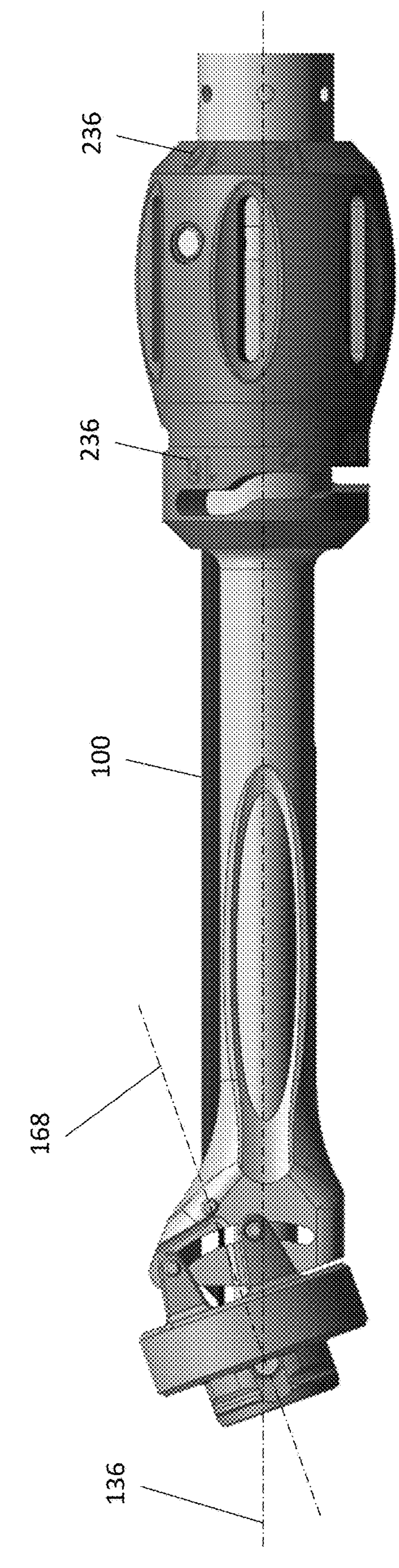
FIG. 4B shows a partial side view of the exemplary reaming device shown in FIGS. 1A and 1B as configured to provide a second offset.

In some embodiments, the reaming device 100 includes a drive square 190 (e.g., a drive interface element) positioned within the bearing 180. In some embodiments, the drive square 190 is generally cylindrical and has an inner bore 192 that is sized so as to allow the drive square 190 to be positioned about the rounded head 140 of the drive shaft 130 such that the drive square 190 can be rotated about the rounded head 140 so as to define the reaming axis 168, such as shown in FIGS. 4A and 4B. In some embodiments, the drive square 190 includes a plurality of generally flat drive surfaces 194 (e.g., torque transmitting surfaces) that are provided to drive a reaming head as will be described hereinafter. In the embodiment shown in FIGS. 1A-1C, the drive square 190 includes four of the drive surfaces 194 that are generally perpendicular to each other and positioned about the perimeter of the drive square 190 in a manner similar to the four sides of a square; in other embodiments, the drive square 190 includes a different number of the drive surfaces 194. In some embodiments, the drive square 190 includes a support region 196 that is sized in a manner complementary to the interior of the bearing 180 such that the support region 196 can be positioned within the bearing 180 in order for the bearing 180 to support the drive square 190 and allow the drive square 190 to freely rotate therein. In some embodiments, the drive square 190 includes a groove 198 that is configured to retain a reaming head as will be described hereinafter with reference to FIGS. 2A-2C. In some embodiments, the drive square 190 includes drive pin holes 200 and 202 that are sized and shaped to receive drive pins therein, as will be described hereinafter, in order to impart rotational movement and torque from the drive shaft 130 to the drive square 190.

In some embodiments, the reaming device 100 includes drive pins 210 and 212. In some embodiments, the drive pins 210 and 212 are positioned within the drive pin holes 200 and 202 of the drive square 190. In some embodiments, the drive pins 210 and 212 are formed separately from the drive square 190 and are permanently mounted into the drive pin holes 200 and 202, such as by welding. In some embodiments, the drive pins 210 and 212 are integrally formed with the drive square 190. In some embodiments, the drive pins 210 and 212 are sized so as to extend into the inner bore 192 of the drive square 190 so as to engage and be positioned within the drive slots 142 of the drive shaft 130, such that rotation of the drive shaft 130 causes corresponding rotation of the drive square 190.

In some embodiments, the reaming device 100 includes retaining rings 220 and 222. In some embodiments, the retaining rings 220 and 222 are commercially available retaining rings such as the type commercialized by McMaster-Carr Supply Company of Robbinsville Township, New Jersey under the trade name SPIRAL INTERNAL RETAINING RINGS, or another type of commercially available retaining ring that is suitable for the retention purposes described herein. In some embodiments, the retaining rings 220 and 222 engage the drive square housing 160 so as to thereby retain the bearing 180 and the drive square 190 in place within the drive square housing.

In some embodiments, the reaming device 100 includes an adjustment knob 230 (e.g., an angle adjustment control element). In some embodiments, the adjustment knob 230 is positioned on and extends about the drive shaft sleeve 114 (e.g., is positioned remotely from the distal end 118 of the housing 110). In some embodiments, the adjustment knob 230 includes an anchoring hole 232 (see FIG. 4A) extending through the adjustment knob 230. In some embodiments, the adjustment knob 230 includes an adjustment slot 234 extending about the perimeter of the adjustment knob 230 in a generally helical manner (e.g., extending both about the perimeter of the adjustment knob 230 and longitudinally along the adjustment knob 230). In some embodiments, the adjustment slot 234 has a stepped helical shape (e.g., includes circumferential portions that extend about the perimeter of the adjustment knob 230 but not longitudinally along the adjustment knob 230, as well as angled portions that extend both about the perimeter of the adjustment knob 230 and longitudinally along the adjustment knob 230). In some embodiments, the adjustment pin 152 of the linkage 150 is positioned within the adjustment slot 234 of the adjustment knob 230 such that rotation of the adjustment knob 230 about the drive axis 136 causes the linkage 150 to move along the drive axis 136 due to the generally helical shape of the adjustment slot 234.

In some embodiments, the adjustment knob 230 includes a series of indicia 236 (see FIGS. 4A-4B) positioned adjacent to the adjustment slot 234 so as to indicate a current angular offset of the reaming device 100. For example, the indicia 236 may include a series of numbers such as 0, 2, 4, 6, 8, 10, 12, 14, and 16, and the alignment of an aligned one of the indicia 236 with the adjustment pin 152 may indicate that the aligned one of the indicia 236 represents the current angular offset of the reaming device 100. In some embodiments, the aligned one of the indicia 236 represents the angular offset of the reaming axis 168 with respect to the drive axis 136. For example, in such an embodiment, an aligned indicia "8" indicates an eight degree offset between the reaming axis 168 and the drive axis 136. In some embodiments, the aligned one of the indicia 236 is indicative of the reaming axis 168 being offset with respect to the drive axis 136 at an angle so as to define a treated bone surface that is angled so as to receive a glenoid baseplate having an augment "size" that corresponds to the aligned one of the indicia 236. For example, in such an embodiment, an aligned indicia "16" may correspond to a glenoid baseplate that is considered to be "size 16", but may have an angular offset that is not equal to sixteen degrees (for example, is equal to twenty degrees). In some embodiments, the adjustment knob

230 is operable to define a minimum offset that is a zero degree offset of the reaming device 100 (e.g., the reaming axis 168 and the drive axis 136 are parallel to one another rather than being offset from one another). For example, with reference to the indicia 236 of the adjustment knob 230 described above, an aligned indicia "0" indicates a zero degree offset between the reaming axis 168 and the drive axis 136.

In some embodiments, the reaming device 100 is configured (e.g., sized and shaped) such that the adjustment knob 230 is positioned outside the body of a patient when the reaming device 100 is positioned so as to ream bone of the patient. As such, in some embodiments, the adjustment knob 230 may be actuated so as to adjust the orientation of the reaming axis 168 (e.g., as will be described hereinafter) while the reaming device 100 is positioned in situ and without a user needing to contact the distal end of the reaming device 100 (e.g., in proximity to a reaming head). In some embodiments, an angle adjustment control element differs from the adjustment knob 230 in specific structure but performs substantially the same function. For example, in some embodiments, an angle adjustment control element includes a user-positionable element that moves linearly along the drive shaft sleeve 114 or along the handle 112 to thereby reposition the linkage 150 or to directly reposition the drive square housing 160. In some embodiments, an angle adjustment control element includes an electronic user interface that is operable to reposition the linkage 150 or the drive square housing 160 (e.g., a user interface element of a surgical computing system that is communicatively coupled to a motor or other actuator to reposition the linkage 150 or the drive square housing 160).

In some embodiments, a ball plunger 240 (e.g., a spring-loaded ball plunger) is positioned within the anchoring hole 232. In some embodiments, the ball plunger 240 is permanently secured within the anchoring hole 232, such as by welding. In some embodiments, the adjustment knob 230 is positioned along the drive shaft sleeve 114 such that the ball plunger 240 is longitudinally aligned (e.g., along the drive axis 136) with the hole array 126. In some embodiments, the ball plunger 240 includes a movable ball 242 that is sized so as to engage holes of the hole array 126.

In some embodiments, rather than including the ball plunger 240, the reaming device 100 includes a different mechanism for engaging holes of the hole array 126.

In some embodiments, the reaming device 100 lacks the hole array 126 and the ball plunger 240, and the adjustment knob 230 is instead operable to be continuously smoothly adjustable over an adjustment range, rather than providing the discrete settings that are provided by the ball plunger 240 and the hole array 126.

In some embodiments, the reaming device 100 includes a drive shaft coupling 250 coupled to the proximal end 132 of the drive shaft 130. In some embodiments, the drive shaft coupling 250 is operable to couple the drive shaft 130 to a tool (e.g., a surgical drill) to thereby cause the drive shaft 130 to rotate about the drive axis 136 within the channel 120.

In some embodiments, the reaming device 100 includes bearings 260 and 262 that are positioned within the housing 110 (e.g., within the handle 112). In some embodiments, the bearings 260 and 262 are positioned so as to be centered on the drive axis 136. In some embodiments, the bearings 260 and 262 are circular ball bearings. In some embodiments, the bearings 260 and 262 support the drive shaft 130 within the housing 110 so as to retain the drive shaft 130 at a desired position within the housing 110 while allowing the drive shaft 130 to be rotated about the drive axis 136.

Figures 2A, 2B, 2C:
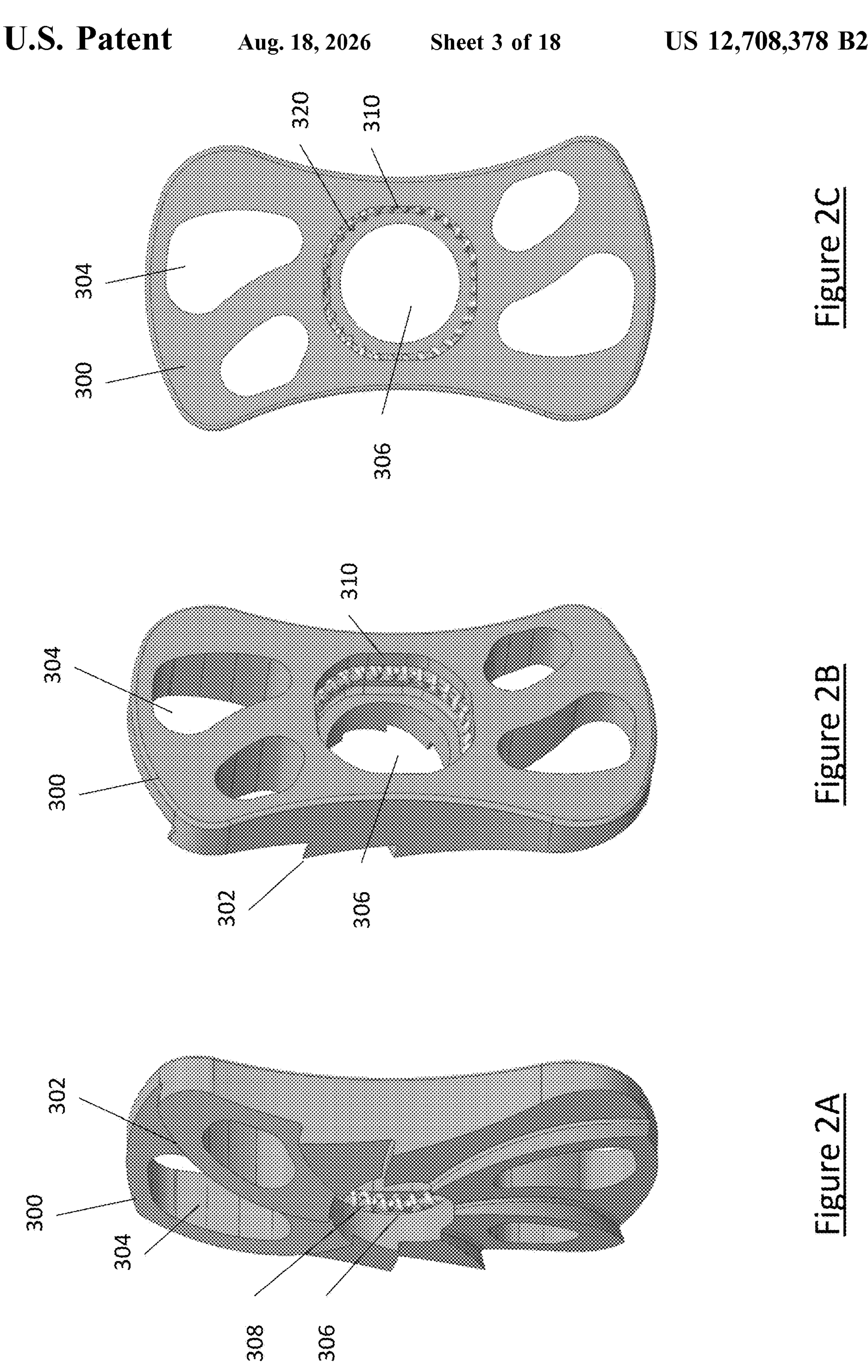
FIG. 2A shows a front perspective view of an exemplary reaming head.
FIG. 2B shows a rear perspective view of the exemplary reaming head shown in FIG. 2A.
FIG. 2C shows a rear view of the exemplary reaming head shown in FIGS. 2A and 2B.

FIG. 2A-2C show a front perspective view, a rear perspective view, and a rear view, respectively, of a reaming head 300 that is configured for use with the reaming device 100. In some embodiments, the reaming head 300 includes reaming elements 302 that are configured to ream bone when the reaming head 300 is driven and the reaming elements 302 are positioned in proximity to the bone. In some embodiments, the reaming head 300 includes spaces 304 that are provided to contain reamed bone tissue when the reaming head 300 is in use. In some embodiments, the reaming head 300 includes a central bore 306 that is sized and shaped so as to allow the reaming head 300 to be positioned over and to engage the drive square 190. In some embodiments, the central bore 306 is sufficiently sized to allow for use of the reaming head 300 on the reaming device 100 while the reaming device 100 is configured to provide an angular offset between the reaming axis 168 and the drive axis 136 of at least a certain amount (e.g., at least twenty degrees). In some embodiments, a groove 308 is formed within the central bore 306. In some embodiments, driven surfaces 310 (e.g., torque receiving surfaces) are formed within the central bore 306. In some embodiments, the driven surfaces 310 are configured (e.g., sized, shaped and provided in a suitable quantity) in a manner complementary to the drive surfaces 194 of the drive square 190 such that, when the reaming head 300 is positioned over the drive square 190, the drive surfaces 194 abut the driven surfaces 310, thereby causing rotation of the drive square 190 to cause corresponding rotation of the reaming head 300.

Figure 3A:
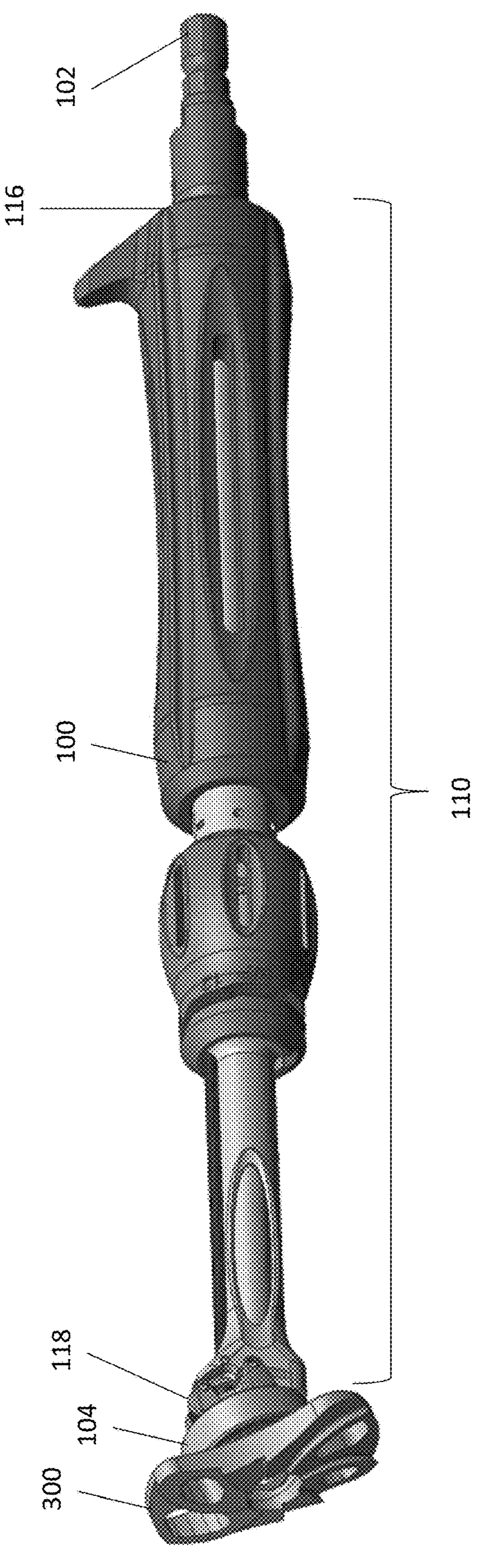
FIG. 3A shows a perspective view of an assembly including the exemplary reaming device shown in FIGS. 1A and 1B assembled with the exemplary head shown in FIGS. 2A-2C.
Figure 3B:
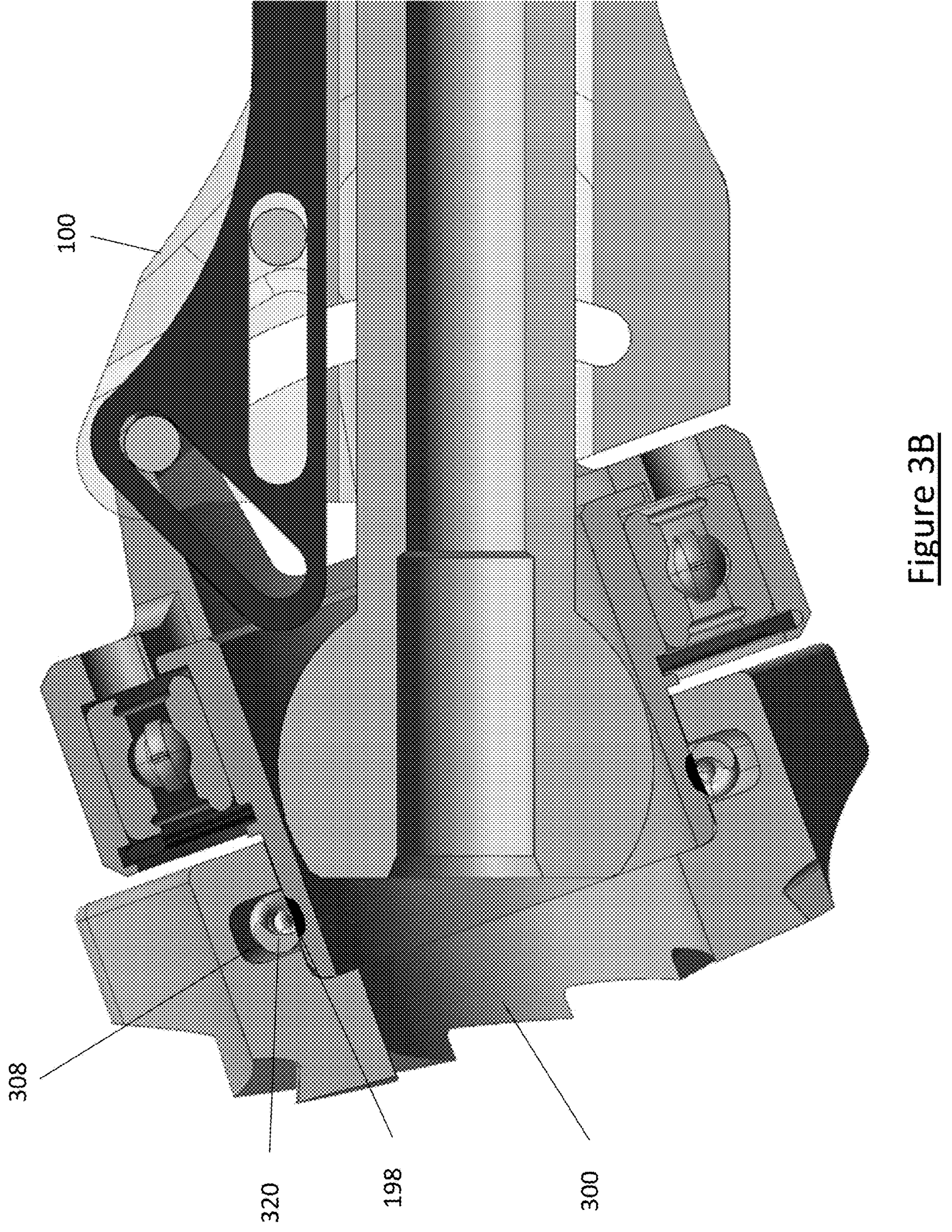
FIG. 3B shows a partial section view of the exemplary assembly shown in FIG. 3A.

In some embodiments, a spring 320 is positioned within the groove 308. In some embodiments, the groove 308, the spring 320, and the groove 198 of the drive square 190 are mutually configured (e.g., sized and shaped) such that, to engage the reaming head 300 to the reaming device 100, a user presses the reaming head 300 over the drive square 190, thereby compressing the spring 320 within the groove 308, until the spring 320 is aligned with the groove 198, at which point the spring 320 is positioned partially within the groove 308 and partially within the groove 198, as shown in FIG. 3B. Once the reaming head 300 is positioned in this manner, the spring 320 retains the reaming head 300 in position, as operation of the reaming device 100 to drive the reaming head 300 does not apply a force in a direction that compresses the spring 320. To remove the reaming head 300 from the reaming device 100, the user then pulls the reaming head 300 away from the reaming device 100, thereby again compressing the spring 320 to remove the spring 320 from the groove 198. FIG. 3A shows a perspective view of an exemplary assembly including the reaming head 300 as assembled to the reaming device 100. FIG. 3B shows a detailed section view of the reaming head 300 as assembled to the reaming device 100, showing the spring 320 as aligned with the groove 198 as described above.

Figure 4C:
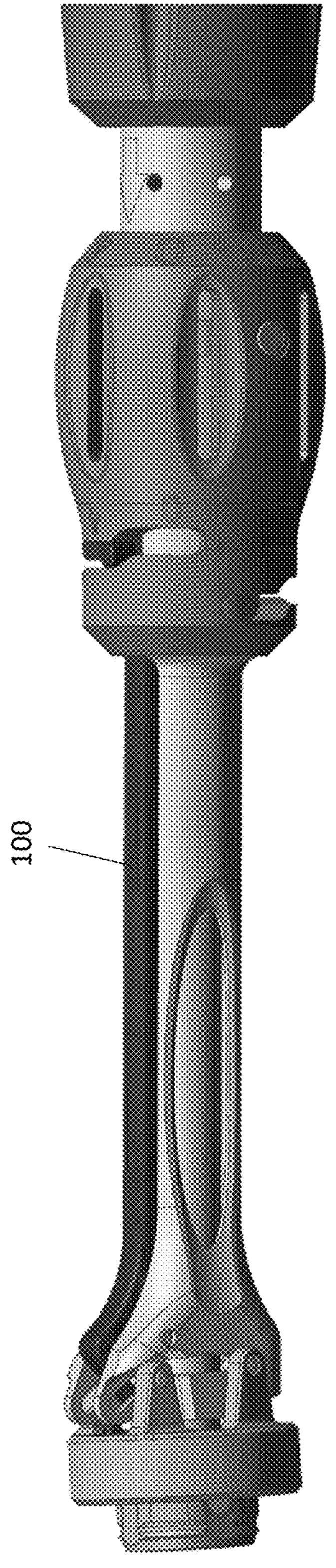
FIG. 4C shows a partial perspective view of the exemplary reaming device shown in FIGS. 1A and 1B as configured as shown in FIG. 4A.
Figure 4C:
Figure 4D:
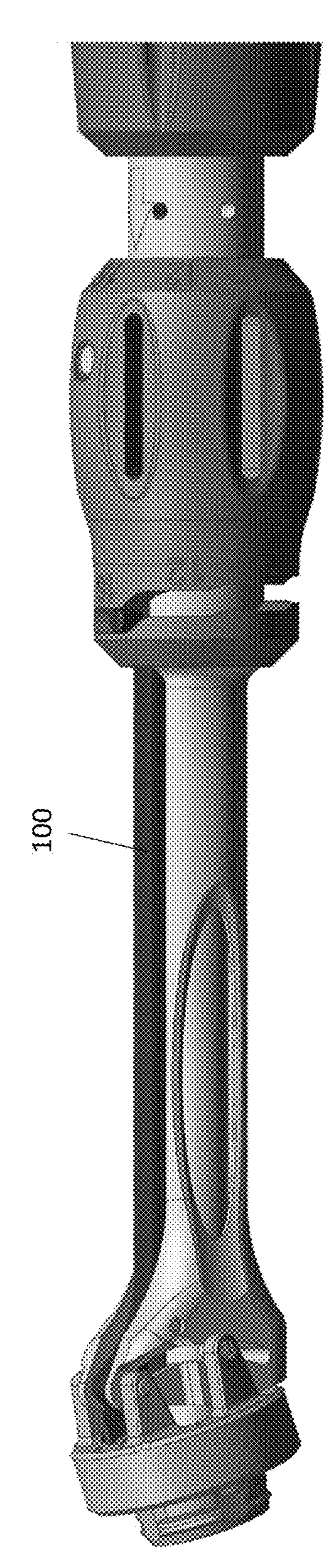
FIG. 4D shows a partial perspective view of the exemplary reaming device shown in FIGS. 1A and 1B as configured as shown in FIG. 4B.
Figures 4E, 4F:
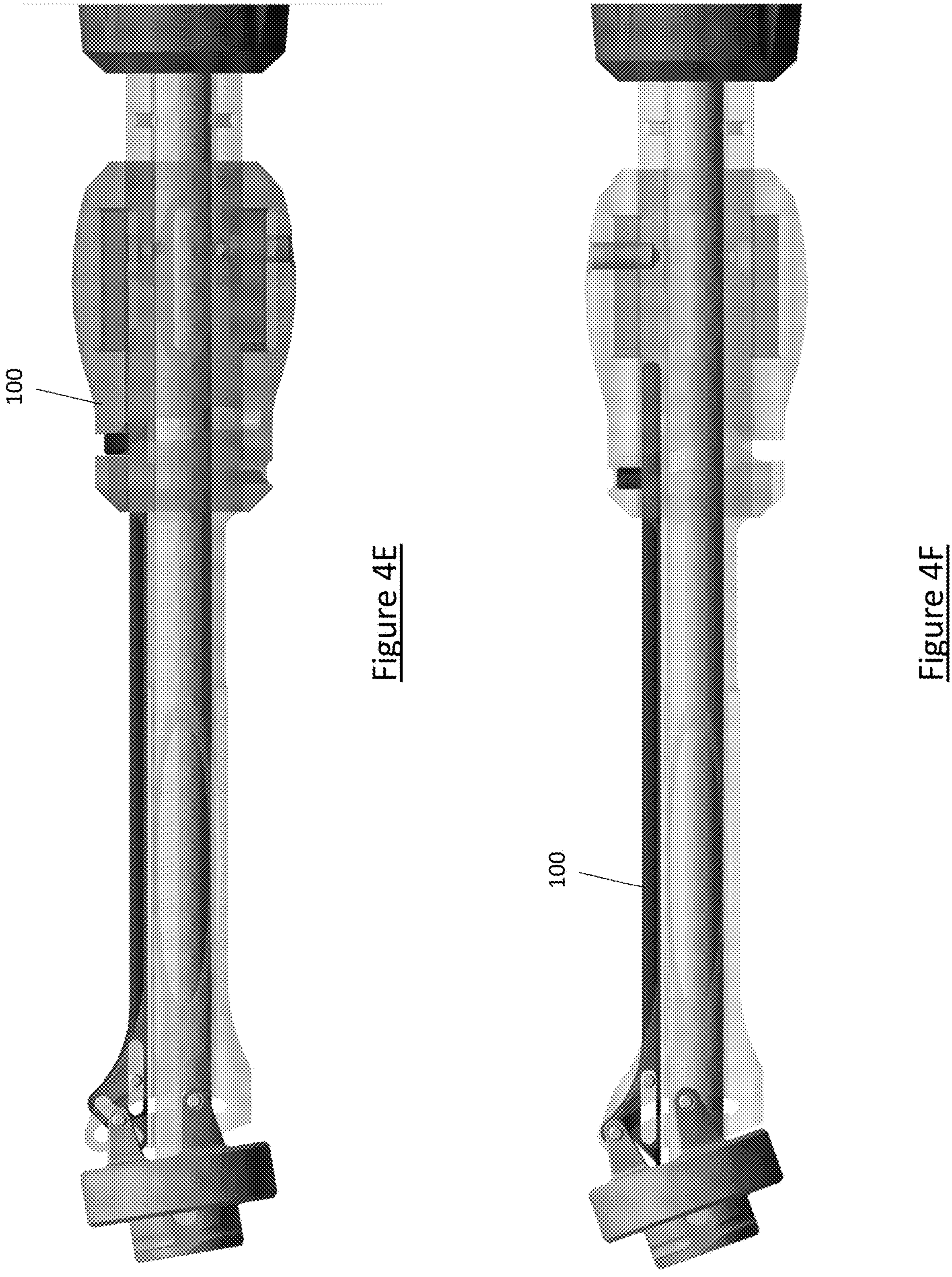
FIG. 4E shows a partially transparent partial side view of the exemplary reaming device shown in FIGS. 1A and 1B as configured as shown in FIG. 4A.
FIG. 4F shows a partially transparent partial side view of the exemplary reaming device shown in FIGS. 1A and 1B as configured as shown in FIG. 4B.
Figures 4G, 4H:
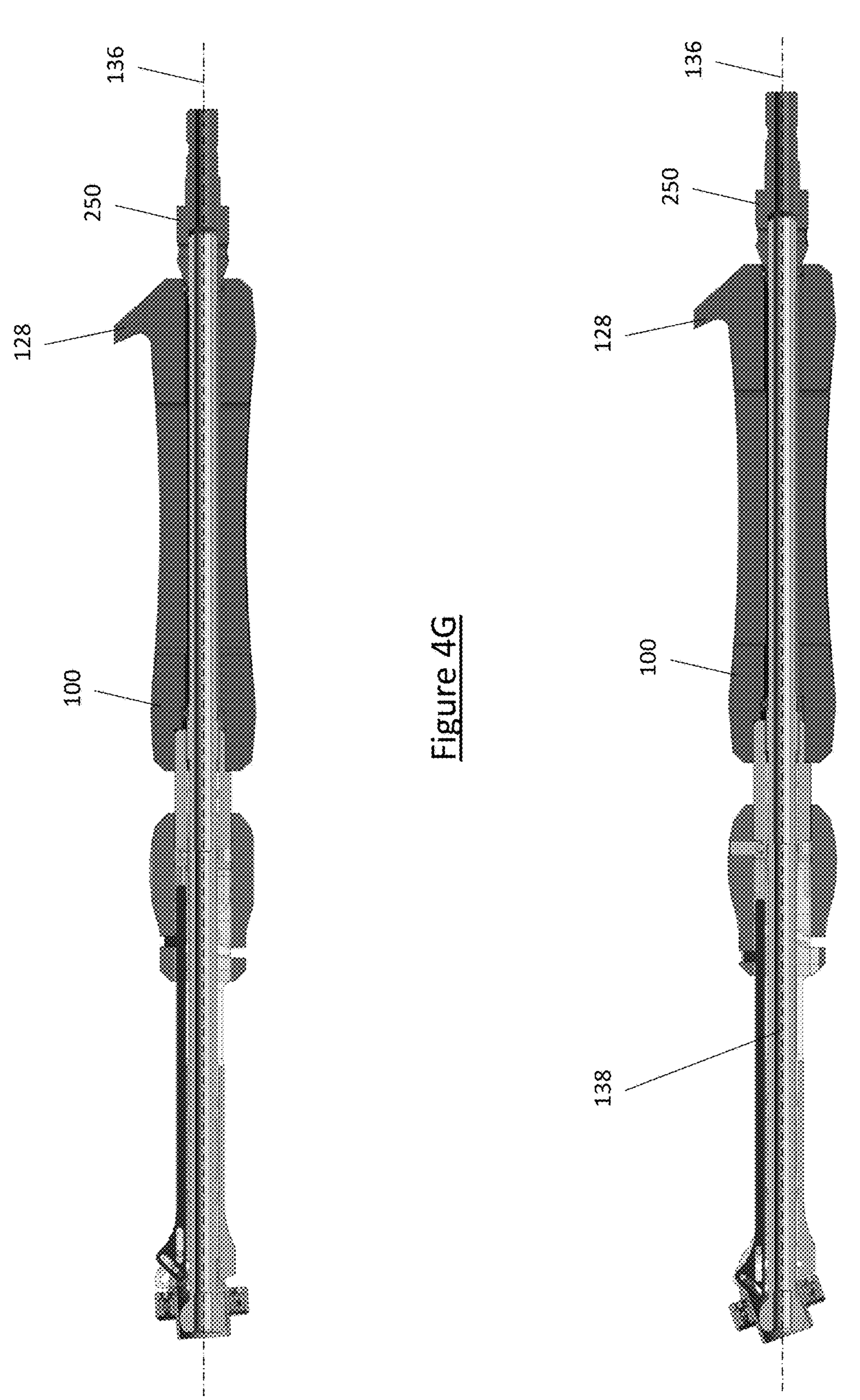
FIG. 4G shows a section view of the exemplary reaming device shown in FIGS. 1A and 1B as configured as shown in FIG. 4A.
FIG. 4H shows a section view of the exemplary reaming device shown in FIGS. 1A and 1B as configured as shown in FIG. 4B.

Referring now to FIGS. 4A-4H, in some embodiments, the adjustment knob 230 can be actuated (e.g., by a user, such as a surgeon) to adjust the orientation of the reaming axis 168 with respect to the drive axis 136, and thereby to adjust the angular offset of a surface formed by operation of the reaming device 100 with respect to a neutral axis defined by a guide pin received within the cannula 138, as follows. FIG. 4A shows a partial side view of the reaming device 100 as configured to orient the reaming axis 168 at a first offset with respect to the drive axis 136. FIG. 4B shows a partial side view of the reaming device 100 as configured to orient the reaming axis 168 at a second offset with respect to the drive axis 136, wherein the second offset is larger than the first offset shown in FIG. 4A. FIG. 4C shows a partial perspective view of the reaming device 100 as configured as shown in FIG. 4A. FIG. 4D shows a partial perspective view of the reaming device 100 as configured as shown in FIG. 4B. FIG. 4E shows a partial side view of the reaming device 100 as configured as shown in FIG. 4A with some elements of the reaming device 100 shown transparently to reveal internal components of the reaming device 100. FIG. 4F shows a partial side view of the reaming device 100 as configured as shown in FIG. 4B with some elements of the reaming device 100 shown transparently to reveal internal components of the reaming device 100. FIG. 4G shows a side section view of the reaming device 100 as configured as shown in FIG. 4A. FIG. 4H shows a side section view of the reaming device 100 as configured as shown in FIG. 4B. FIGS. 4A, 4C, 4E, and 4G show the reaming device 100 having a first offset between the reaming axis 168 and the drive axis 136 that is about five degrees, and FIGS. 4B, 4D, 4F, and 4H show the reaming device 100 having a larger second offset between the reaming axis 168 and the drive axis 136 that is about twenty degrees. The specific first and second offsets shown in FIGS. 4A-4H are only selected for illustrative purposes, and the reaming device 100 may be operable, either in the specific embodiment shown herein or in other embodiments, to provide variable offsets that may be as small as zero degrees (i.e., the reaming axis 168 is aligned with the drive axis 136) or as large as thirty degrees.

Continuing to refer to FIGS. 4A-4H, in some embodiments, at any given first position (where the term "first" is used only for purposes of description herein and does not refer to any particular sequence during actual use of the exemplary reaming device 100) of the adjustment knob 230 (e.g., as shown in FIG. 4A), the ball plunger 240 is positioned such that the movable ball 242 engages one of the holes of the hole array 126. For example, FIG. 4C shows the reaming device 100 with the adjustment knob 230 positioned such that the movable ball 242 is engaged with one of the holes of the hole array 126 so as to align the adjustment pin 152 of the linkage 150 with one of the indicia 236 that indicates "4" (e.g., is indicative of the reaming device 100 being configured so as to ream tissue in a manner suitable to receive a glenoid component that corresponds to the "4" indication.

In some embodiments, to adjust the orientation of the reaming axis 168 with respect to the drive axis 136, a user rotates the adjustment knob 230 with respect to the drive shaft sleeve 114. Because of the generally helical shape of the adjustment slot 234, together with the manner in which the position of the linkage 150 is constrained by the first dowel pin 170 and the second dowel pin 172, such rotation causes the linkage 150 to move longitudinally along the drive shaft sleeve 114 (e.g., in a direction parallel to the drive axis 136). As discussed above, the second dowel pin 172 is fixed in the first transverse hole 162, and is slidably positioned within the angled slot 156 of the linkage 150 and within the curved slot 122 of the of the drive shaft sleeve 114. Consequently, longitudinal motion of the linkage 150 causes the second dowel pin 172 to slide along the angled slot 156 and the curved slot 122. As a result, such motion of the second dowel pin 172 causes corresponding motion of the drive square housing 160, which must move together with the second dowel pin 172 due to the second dowel pin 172 being fixed within the first transverse hole 162. Because the bearing 180 and the drive square 190 are fixed in position within the drive square housing 160, these elements move as well, thereby adjusting the reaming axis 168.

Following rotation of the adjustment knob 230 as described above, the adjustment knob 230 may be positioned in a second position (where, as for the term "first" above, the term "second" is used only for purposes of description herein and does not refer to any particular sequence during actual use of the exemplary reaming device 100), in which the ball plunger 240 is positioned such that the movable ball 242 engages one of the holes of the hole array 126 that is a different one of the holes than was engaged by the movable ball 242 when the adjustment knob 230 was positioned in the first position. For example, FIG. 4D shows the reaming device 100 with the adjustment knob 230 positioned such that the movable ball 242 is engaged with one of the holes of the hole array 126 so as to align the adjustment pin 152 of the linkage 150 with one of the indicia 236 that indicates "16" (e.g., is indicative of the reaming device 100 being configured so as to ream tissue in a manner suitable to receive a glenoid component that corresponds to the "16" indication.

The description above refers to a first position and a second position of the adjustment knob 230. However, the hole array 126 may include any different number of holes, and the adjustment knob 230 may then be capable of being adjusted to a corresponding any different number of positions.

Figure 5A:
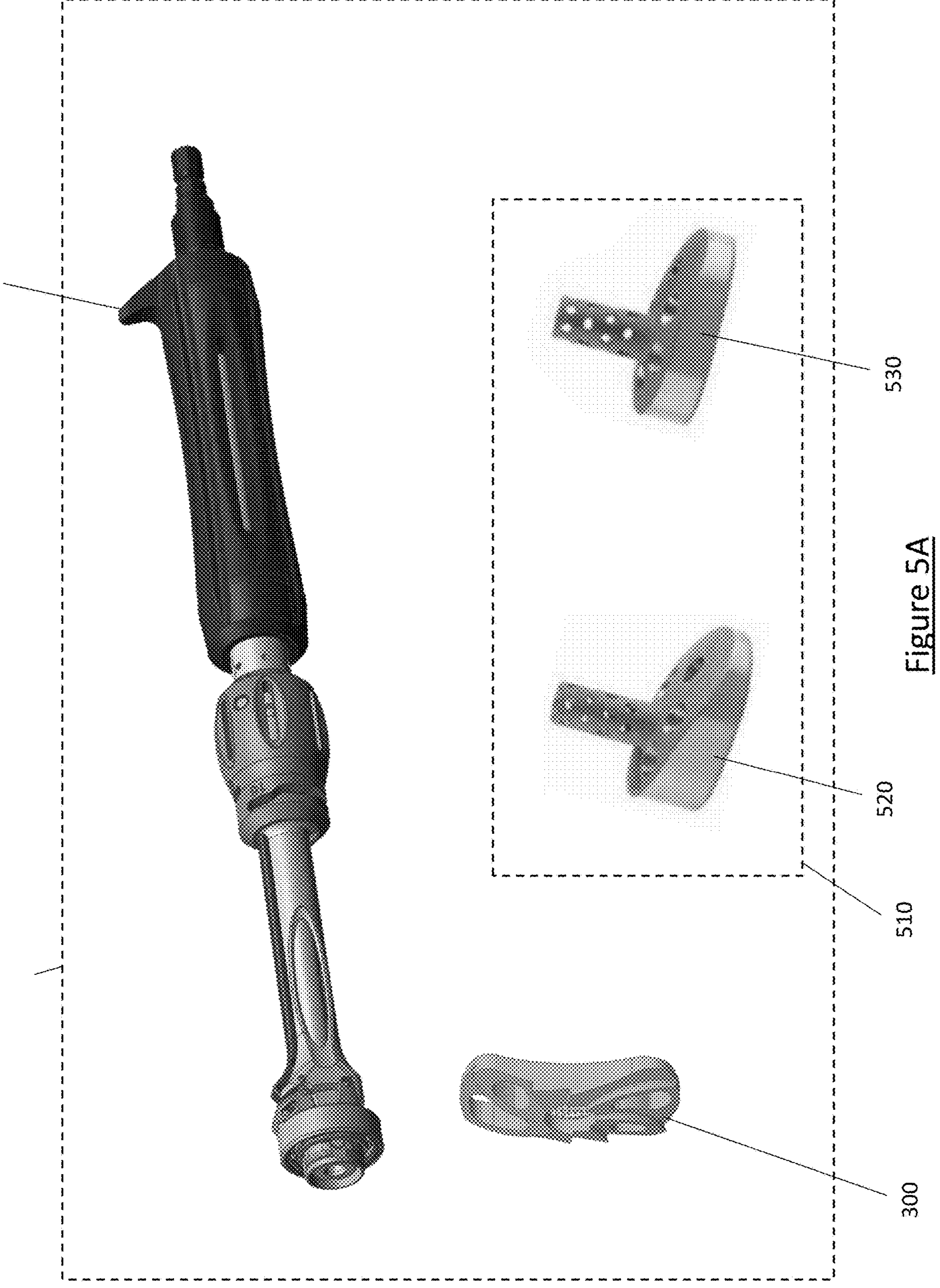
FIG. 5A shows elements of an exemplary kit including the exemplary reaming device shown in FIGS. 1A and 1B.

In some embodiments, the reaming device 100 is provided as part of a kit 500 that also includes other components that are used to perform a shoulder arthroplasty on a patient. FIG. 5A shows some elements of an exemplary kit 500. It should be understood that the elements of the kit 500 shown in FIG. 5A are not exhaustive, and that practical implementations of kits including the reaming device 100 may include additional elements not shown in FIG. 5A. In some embodiments, the kit 500 includes the reaming device 100 and the reaming head 300 described above. In some embodiments, the kit includes more than one different version of the reaming head 300 (e.g., versions sized differently to provide the option to select a version of the reaming head 300 that is tailored to the size of the patient's anatomy, versions made from different materials or having different finishes to provide the option to select a version of the reaming head 300 that is suitable for characteristics of the patient's bone, etc.).

Figure 5B:
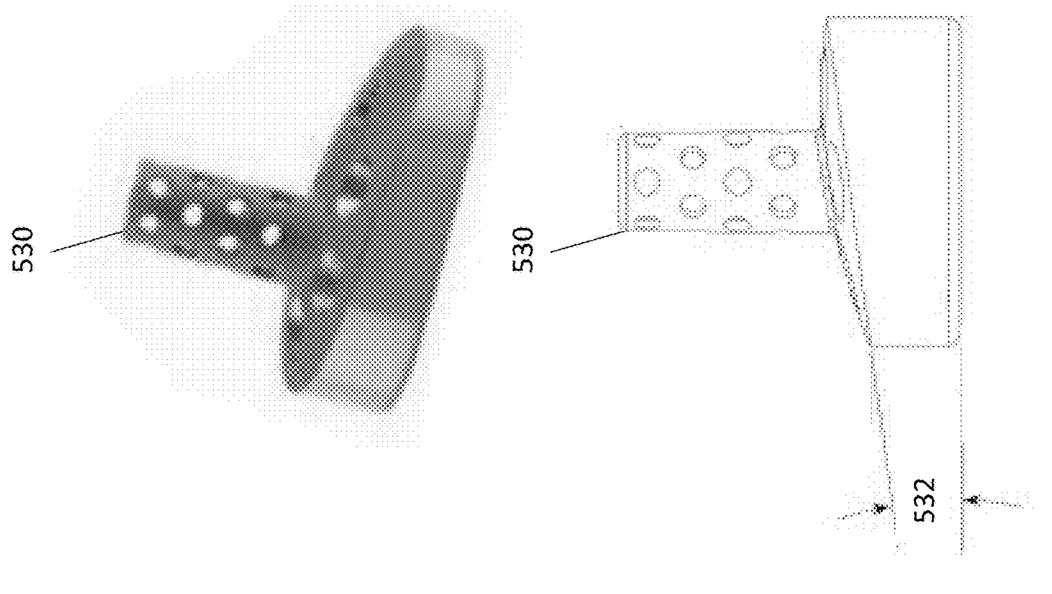
FIG. 5B shows additional views of elements of the exemplary kit shown in FIG. 5A.
Figure 5B:
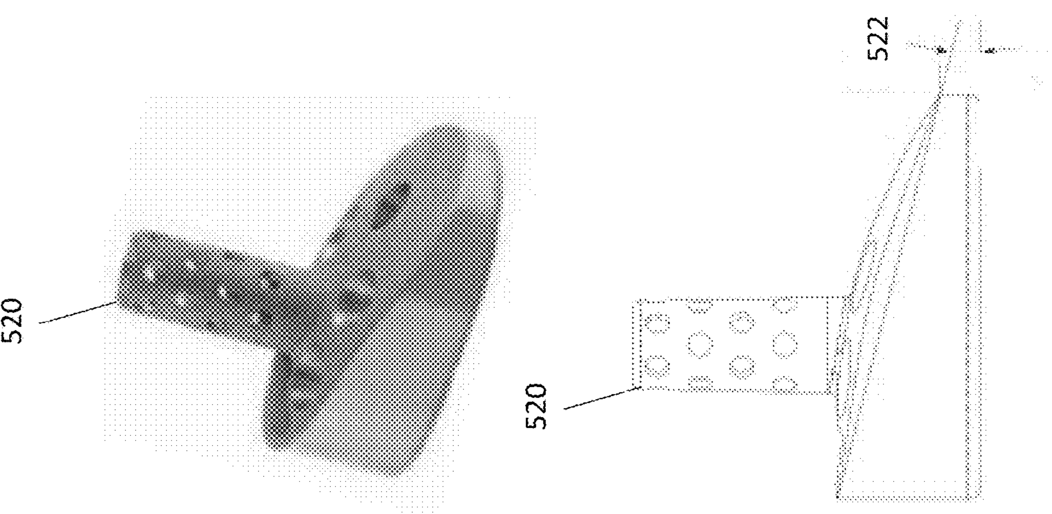

In some embodiments, the kit 500 includes a glenoid component set 510 including glenoid components 520 and 530, each of which is adapted to be mounted to a treated glenoid of a patient and to thereby form part of a glenoid side of a shoulder prosthesis. FIGS. 5A and 5B show the glenoid component set 510 including two of the glenoid components 520 and 530, but in other embodiments, the glenoid component set 510 may include a greater number of the glenoid components 520 and 530 that may be provided as described herein. In some embodiments, the glenoid component set 510 includes at least one glenoid component that is configured to form part of an anatomical shoulder prosthesis. In some embodiments, the glenoid component set 510 includes at least one glenoid component that is configured to form part of a reverse shoulder prosthesis.

FIG. 5B shows additional views of the glenoid components 520 and 530. In some embodiments, the glenoid components 520 and 530 are differently sized from one another. In some embodiments, the glenoid components 520 and 530 provide augment angles 522 and 532, respectively, that differ from one another (e.g., the augment angle 532 is larger than the augment angle 522), and thus are suitable for fixation to patient's glenoids that have had bone reamed at a different angle (e.g., through the use of the reaming device 100 as configured to provide a differing offset angles between the reaming axis 168 and the drive axis 136. In the embodiment shown in FIG. 5B, the augment angle 522 is 8 degrees and the augment angle 532 is 10 degrees, but these specific augment angles are only exemplary and the glenoid component set 510 included in the kit 500 may include glenoid components 520 and 530 having various other angles. In some embodiments, the glenoid component set 510 includes the glenoid components 520 and 530 that are the glenoid components commercialized by Exactech, Inc. of Gainesville, Florida under the trade name EQUINOXE AUGMENTED REVERSE GLENOID IMPLANTS.

In some embodiments, the reaming device 100 included in the kit 500 includes the adjustment knob 230 having settings that correspond to specific ones of the glenoid components 520 and 530 in the glenoid component set 510. For example, in some embodiments, the glenoid component 520 is considered to be a "size 10" glenoid component, wherein "size 10" refers to the magnitude of the augment angle 522, and a first one of the indicia 236 indicates "10" or "size 10" to indicate that, when the adjustment pin 152 is aligned with the first one of the indicia 236, the reaming device 100 is configured to provide an angular offset between the reaming axis 168 and the drive axis 136 that will ream a patient's glenoid at a suitable angle to prepare for fixation of the glenoid component 520. Similarly, for example, in some embodiments, the glenoid component 530 is considered to be a "size 14" glenoid component, wherein "size 14" refers to the magnitude of the augment angle 532, and a second one of the indicia 236 indicates "14" or "size 14" to indicate that, when the adjustment pin 152 is aligned with the second one of the indicia 236, the reaming device 100 is configured to provide an angular offset between the reaming axis 168 and the drive axis 136 that will ream a patient's glenoid at a suitable angle to prepare for fixation of the glenoid component 530. The specific size designations described are only exemplary and other embodiments may indicate correspondence between the glenoid components of the glenoid component set 510 and the settings of the reaming device 100 using other identifiers without departing from the broader principles embodied by the exemplary embodiments described herein.

Figures 6A, 6B:
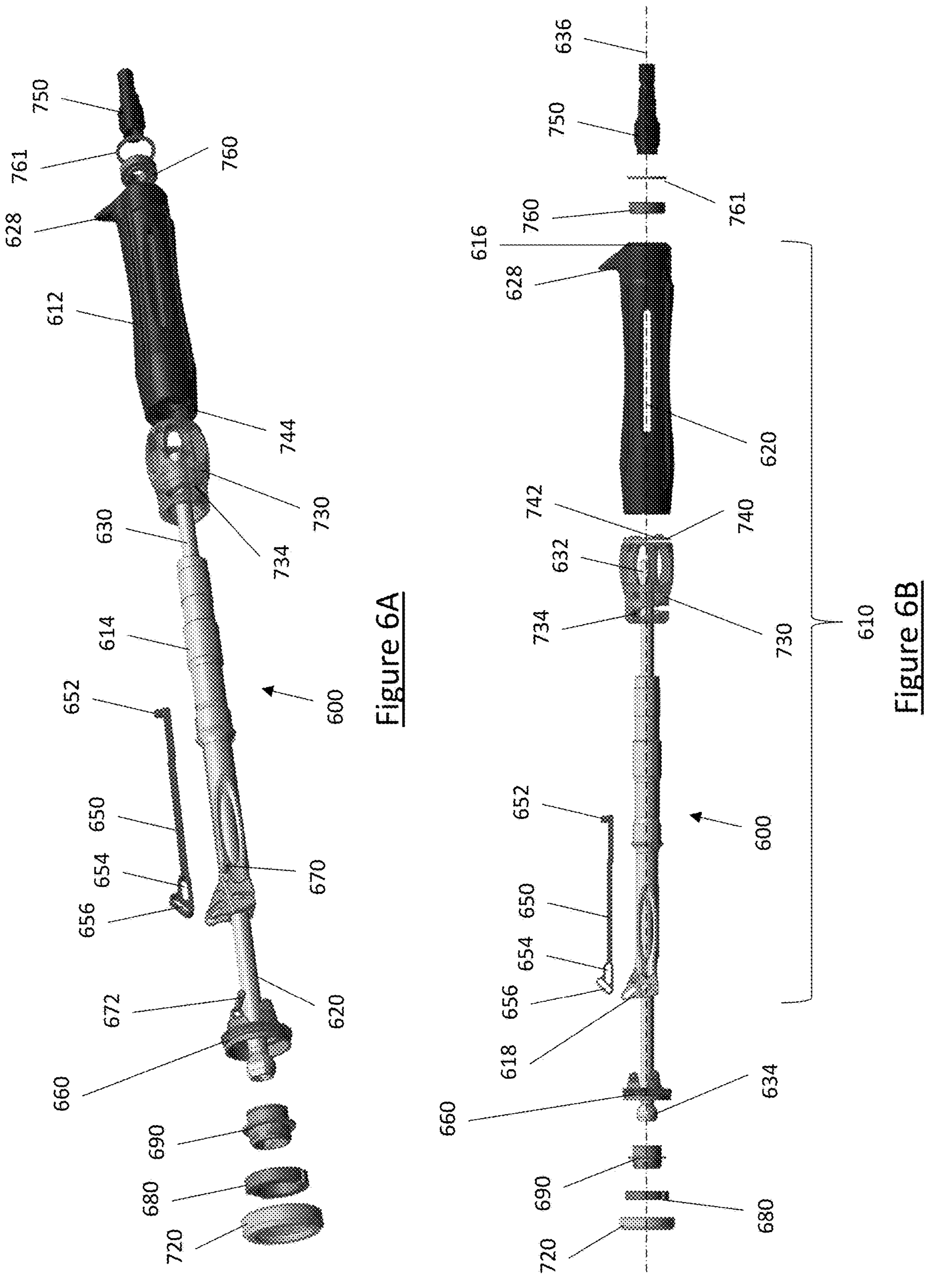
FIG. 6A shows an exploded perspective view of an exemplary reaming device.
FIG. 6B shows an exploded side view of the exemplary reaming device shown in FIG. 6A.
Figure 6C:
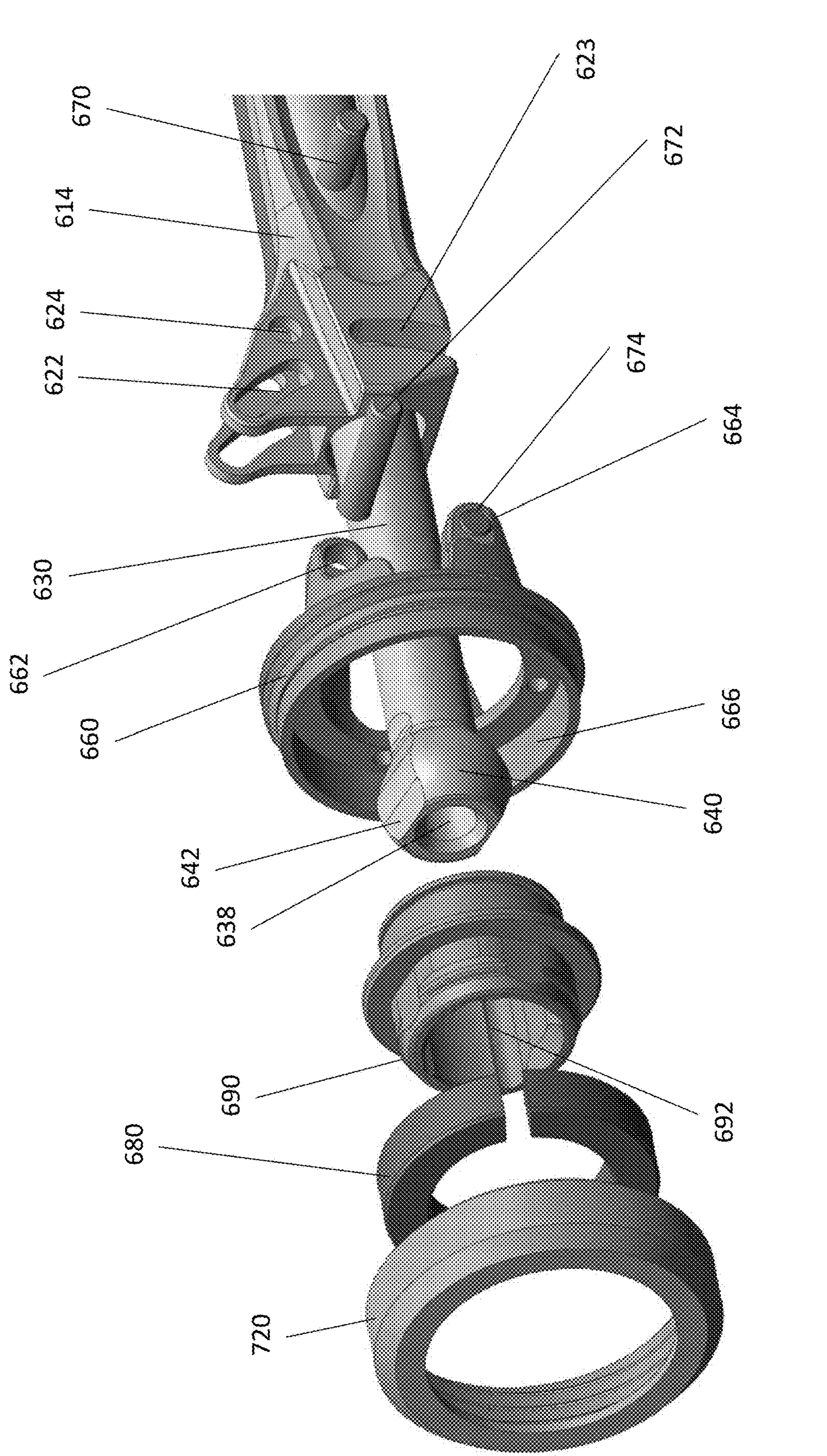
FIG. 6C shows an exploded perspective view of the distal end of the exemplary reaming device shown in FIG. 6A.
Figure 6D:
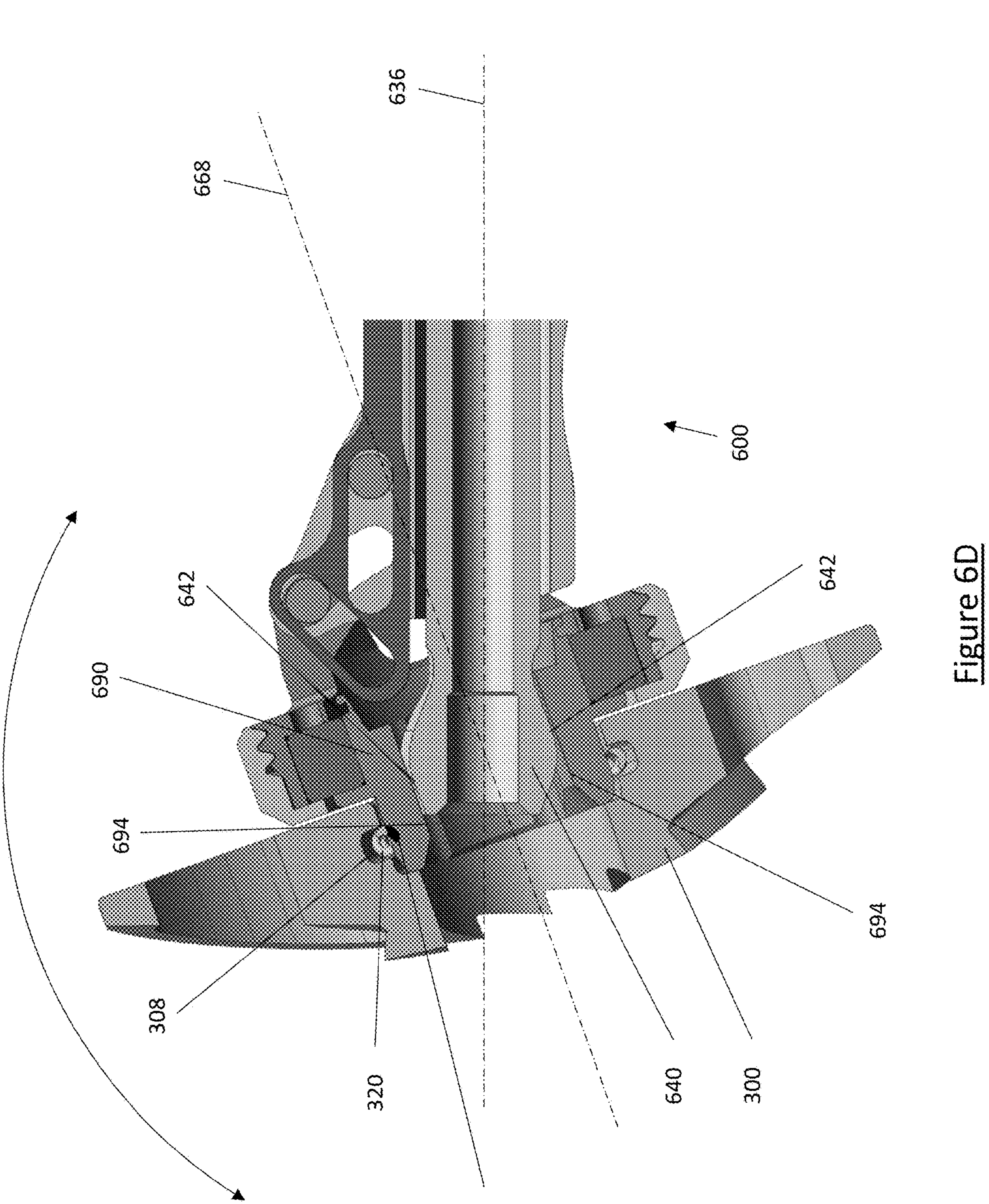
FIG. 6D shows a cross-sectional view of the distal end of the exemplary reaming device shown in FIG. 6A.
Figures 6E, 6F:
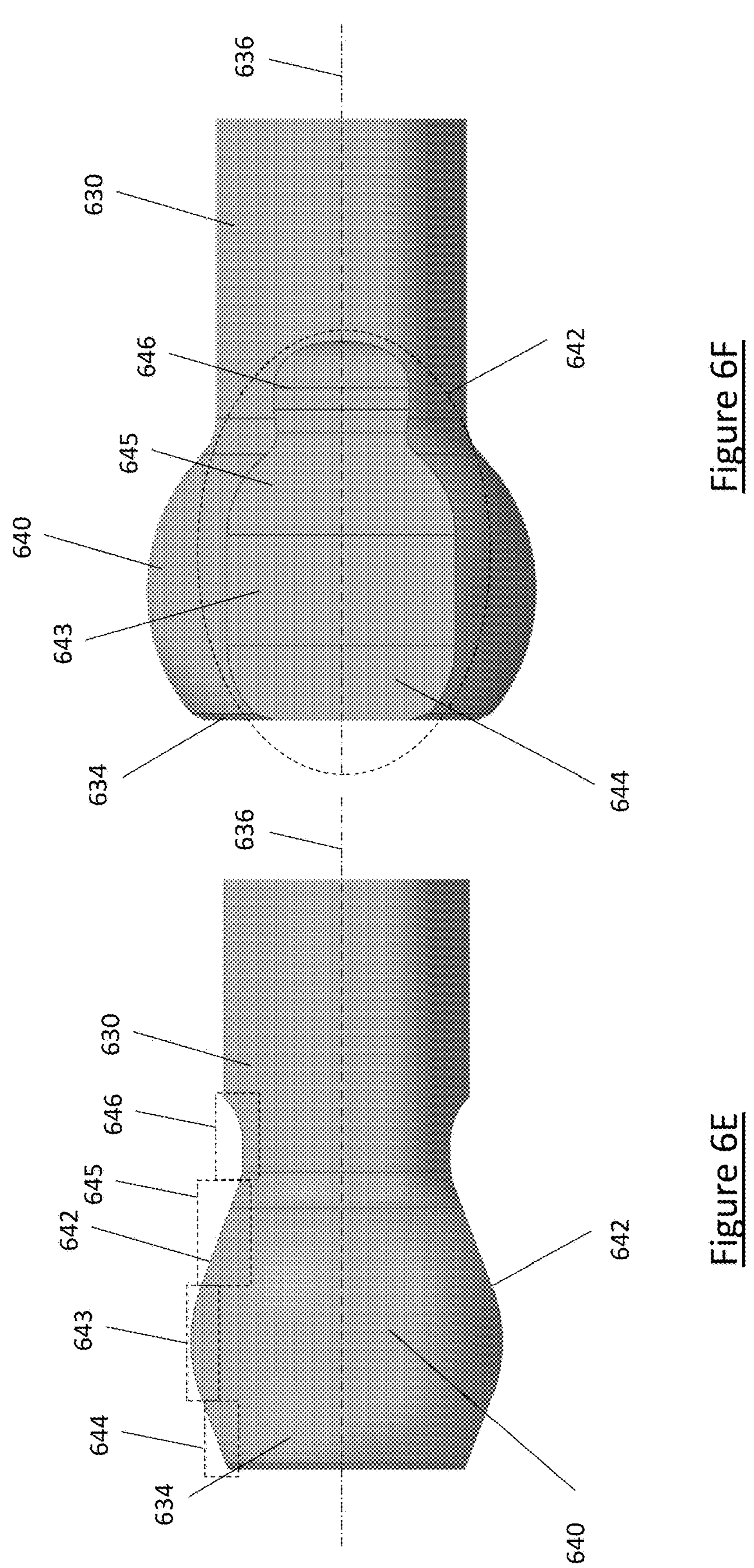
FIG. 6E shows a detailed view of a distal end of a drive shaft of the exemplary reaming device shown in FIG. 6A from a first perspective.
FIG. 6F shows a detailed view of the distal end of a drive shaft of the exemplary reaming device shown in FIG. 6A from a second perspective that is perpendicular to the first perspective shown in FIG. 6E.

FIGS. 6A-6H show an embodiment of a reaming device 600. FIG. 6A shows a perspective exploded view of the reaming device 600. FIG. 6B shows a side exploded view of the reaming device 600. FIG. 6C shows an exploded view of elements of the distal end of the reaming device 600. FIG. 6D shows a section view of the distal end of the reaming device 600. FIG. 6E shows a detailed view of a distal end of a drive shaft of the reaming device 600 from a first viewing angle. FIG. 6F shows a detailed view of a distal end of the drive shaft shown in FIG. 6E from a second viewing angle that is perpendicular to the first viewing angle. In some embodiments, the reaming device 600 is substantially similar to the reaming device 100 described above other than in the specific respects described hereinafter. Elements of the reaming device 600 shown in FIGS. 6A-6D but not specifically described herein should be understood to have substantially the same function as the corresponding elements of the reaming device 100 described above. In some embodiments, the reaming device 600 may be included in the kit 500 in place of the reaming device 100 without altering the overall use or function of the kit 500.

Referring to FIGS. 6A and 6B, the reaming device 600 includes a housing 610 that is formed by a handle 612 and a drive shaft sleeve 614. The housing 610 includes a proximal end 616 and a distal end 618. A channel 620 extends through the housing 610 (e.g., through the handle 612 and the drive shaft sleeve 614. The channel 620 defines a drive axis 636. A drive shaft 630 extends through the channel 620. A cannula 638 is formed within the drive shaft 630. A drive shaft coupling 750 is coupled to a proximal end of the drive shaft 630.

Continuing to refer to FIGS. 6A and 6B, in some embodiments, the reaming device 600 includes a bearing 760 that is positioned within the housing 610 (e.g., within the handle 612). In some embodiments, the bearing 760 positioned so as to be centered on the drive axis 636. In some embodiments, the bearing 760 is a circular ball bearing. In some embodiments, the bearing 760 supports the drive shaft 630 within the housing 610 so as to retain the drive shaft 630 at a desired position within the housing 610 while allowing the drive shaft 630 to be rotated about the drive axis 636. In some embodiments, a retaining ring 761 is positioned at and secured within the proximal end 616 of the housing 610 so as to retain the bearing 760 and the drive shaft 630 within the housing 610.

Continuing to refer to FIGS. 6A and 6B, in some embodiments, the reaming device 600 includes an adjustment knob 730 that is positioned on the drive shaft sleeve 614 and is operable to adjust the angular offset provided by the reaming device 600 in a similar manner to that described above with reference to the adjustment knob 230. In some embodiments, the adjustment knob 730 includes an adjustment slot 734 that is substantially similar to the adjustment slot 234 described above. In some embodiments, the adjustment knob 730 includes a flange 740 that extends from the end of the adjustment knob 730 that faces toward the handle 612 and is resiliently flexible (e.g., can be deflected by application of force but returns to its original position). In some embodiments, a protrusion 742 extends from the flange 740 toward the handle 612. In some embodiments, a series of dimples 744 are formed in the end of the handle 612 that faces toward the adjustment knob 730 and are arrayed circumferentially about the drive axis 636 so as to be radially aligned with the protrusion 742. In some embodiments, when the adjustment knob 730 is rotated about the drive shaft sleeve 614 to thereby adjust the angular offset provided by the reaming device 600, the protrusion 742 moves along the series of dimples 744. In some embodiments, each of the dimples 744 corresponds to a different discrete setting of an angular offset of the reaming device 600, and the flange 740 is positioned so as to provide each discrete setting when the protrusion 742 is positioned in the corresponding one of the dimples 744 in the same manner as described above with reference to the hole array 126 and the ball plunger 240. In some embodiments, when the protrusion 742 is rotationally aligned with one of the dimples 744, the resiliently flexible character of the flange 740 causes the protrusion 742 to be urged toward and to sit within the one of the dimples 744. Similarly, in some embodiments, the flange 740 must be flexed away from the handle 612 to allow the protrusion 742 to pivot away from the one of the dimples 744, thereby preventing inadvertent movement of the adjustment knob 730 away from a selected position, and providing a "locked" sensation to a user when the adjustment knob 730 is correctly positioned. Accordingly, in some embodiments, the protrusion 742 and the series of dimples 744 provide similar adjustment functionality to the reaming device 600 as the ball plunger 240 and the hole array 126 provide to the reaming device 100 as described above.

Continuing to refer to FIGS. 6A and 6B, in some embodiments, the reaming device 600 includes a linkage 650 that includes an adjustment pin 652, an axial slot 654, and an angled slot 656. In some embodiments, when the reaming device 600 is assembled, the adjustment pin 652 is positioned within the adjustment slot 734 of the adjustment knob 730 such that rotation of the adjustment knob 730 causes linear movement of the linkage 650 in the manner described above with reference to the linkage 150.

Referring now to FIG. 6C, in some embodiments, the drive shaft sleeve 614 includes a transverse hole 624 that is substantially similar to the transverse hole 124 described above. In some embodiments, the reaming device 600 includes a drive square housing 660 that is substantially similar to the drive square housing 160 other than as will be described hereinafter. In some embodiments, the 660 includes a first transverse hole 662, a second transverse hole 664, and a bore 666 that are substantially similar to the corresponding elements of the drive square housing 160 described above. In some embodiments, the bore 666 defines a reaming axis 668 as described above with reference to the bore 166. In some embodiments, the drive shaft sleeve 614 includes a first curved slot 622 and a second curved slot 623 that correspond to different portions of the curved slot 122 described above.

Continuing to refer to FIG. 6C, in some embodiments, the reaming device 600 includes a first dowel pin 670, a second dowel pin 672, and a third dowel pin 674. In some embodiments, the first dowel pin 670 is positioned within the transverse hole 624 of the drive shaft sleeve drive shaft sleeve 614 and within the axial slot 654 of the linkage 650 so as to constrain movement of the linkage 650 in the same manner as described above with reference to the first dowel pin 170. In some embodiments, the second dowel pin 672 is positioned within the first transverse hole 662 of the drive square housing 660 and within the curved slot 622 of the drive shaft sleeve 614 so as to allow for adjustment of the drive square housing 660 to orient the reaming axis 668 as described above. In some embodiments, the third dowel pin 674 is positioned within the second transverse hole 664 of the drive square housing 660 and within the second curved slot 623 of the drive shaft sleeve 614 so as to allow for adjustment of the drive square housing 660 to orient the reaming axis 668 as described above.

Referring now to FIGS. 6A-6F, in some embodiments, the drive shaft 630 has a proximal end 632 and a distal end 634. In some embodiments, the drive shaft 630 includes a rounded head 640 formed at the distal end 634. In some embodiments, drive faces 642 (e.g., torque transmitting surfaces) are formed on the rounded head 640. In some embodiments, the drive faces 642 are surfaces that define a constant cross-section across the rounded head 640 when viewed in a transverse direction (see, e.g., FIG. 6E), and follow the rounded contour of the rounded head 640 along the axial direction of the drive shaft 630 (sec, e.g., FIG. 6F). In some embodiments, each of the drive faces 642 includes a central portion 643 that has a cross-section of a circular arc (e.g., as viewed in FIG. 6E). In some embodiments, each of the drive faces 642 includes a first planar portion 644 distal to the central portion 643 and a second planar portion 645 proximal to the central portion 643, both of which are generally planar and have a cross-section of a line (e.g., as viewed in FIG. 6E). In some embodiments, each of the drive faces 642 includes a transition region 646 that defines a transition between the drive face 642 and the generally circular cross-section of the drive shaft 630, and is concave when viewed in cross-section (e.g., as viewed in FIG. 6E) to allow for proper clearance as will be shown below. In some embodiments, the drive faces 642 are operable to transmit torque from the drive shaft 630 to a reaming head as will be described hereinafter. In some embodiments, the rounded head 640 includes two of the drive faces 642.

Continuing to refer to FIGS. 6A-6D, in some embodiments, the reaming device 600 includes a drive square 690. In some embodiments, the drive square 690 includes an inner bore 692 that is sized so as to allow the drive square 690 to be positioned about the rounded head 640 of the drive shaft 630 such that the drive square 690 rotates about the rounded head 640 with the drive square housing 660 so as to define the reaming axis 668, as described above with reference to the drive square 190. In some embodiments, the drive square 690 includes a plurality of generally flat driven surfaces 694 (e.g., torque receiving surfaces). In some embodiments, the drive square 690 includes the same quantity of the driven surfaces 694 as the quantity of the drive faces 642 included in the drive shaft 630. In some embodiments, the drive square 690 includes two driven surfaces 694. In some embodiments, the driven surfaces 694 are flat or substantially flat surfaces that are configured (e.g., sized and shaped) to abut the drive faces 642.

Figures 6G, 6H:
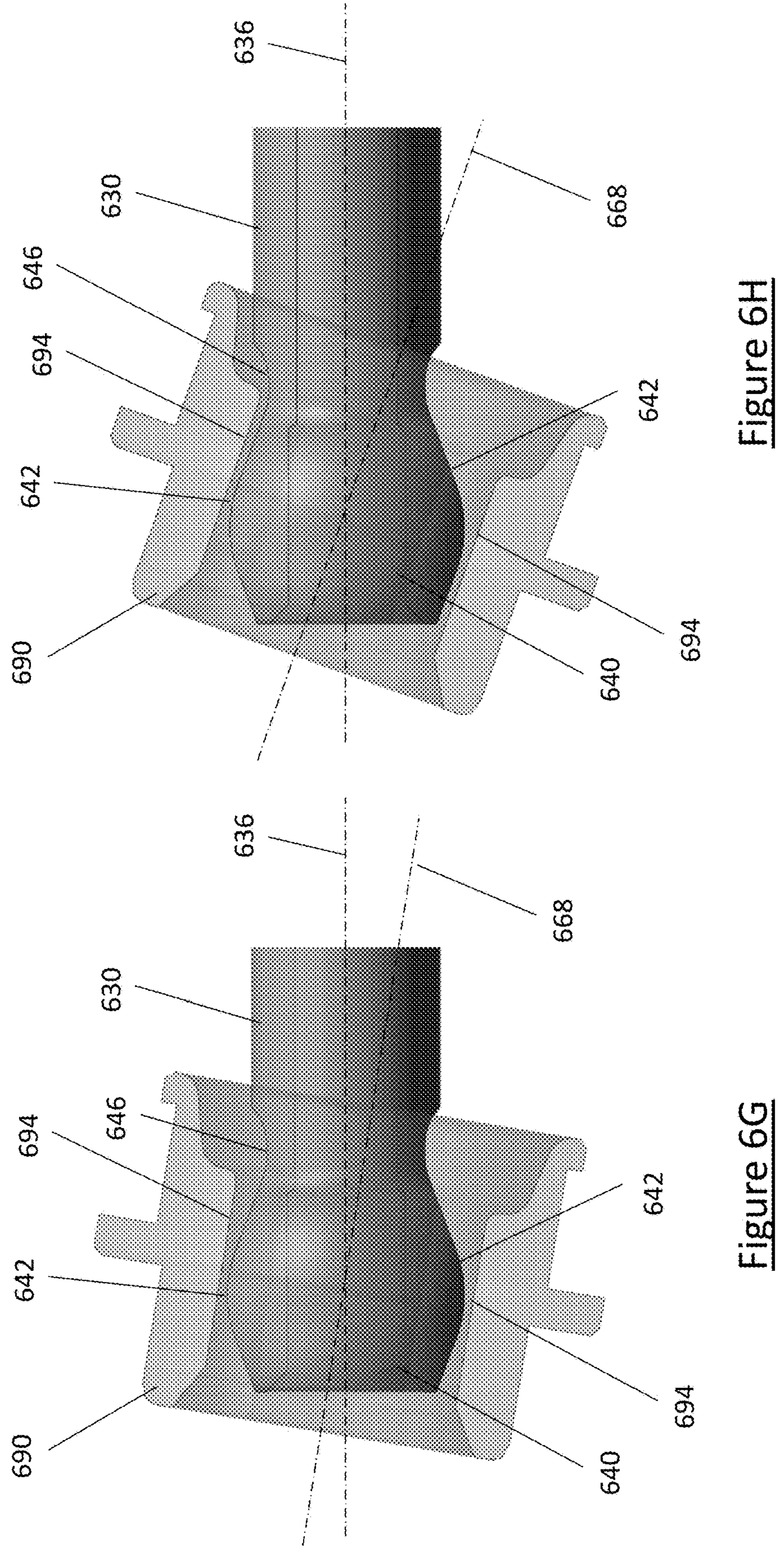
FIG. 6G shows a view of the distal end of the drive shaft and a drive square of the exemplary reaming device shown in FIG. 6A, in which the drive square is positioned to provide a first angular offset.
FIG. 6H shows a view of the distal end of the drive shaft and a drive square of the exemplary reaming device shown in FIG. 6A, in which the drive square is positioned to provide a second angular offset that is greater than the first angular offset shown in FIG. 6G.

FIGS. 6G and 6H show the distal end of the drive shaft 630 and the drive square 690, with the drive square 690 rendered transparently to allow visualization of the interfacing elements of the drive shaft 630 and the drive square 690. In some embodiments, the driven surfaces 694 and the drive faces 642 are shaped in a complementary manner to one another such that, when the drive square housing 660 and the drive square 690 are pivoted with respect to the drive shaft sleeve 614 so as to adjust the orientation of the reaming axis 668, the driven surfaces 694 slide along the contours of the drive faces 642 in the directions denoted by an arc in FIG. 6D, while remaining in contact with the drive faces 642. For example, FIGS. 6G and 6H show side views of the drive square 690 and the rounded head 640 of the drive shaft 630, with the drive square 690 rendered in a translucent manner to show the interaction between the drive square 690 and the rounded head 640. FIG. 6G shows the drive square 690 positioned to define a first offset between the reaming axis 668 and the drive shaft axis 636, and FIG. 6H shows the drive square 690 positioned to define a larger second offset between the reaming axis 668 and the drive shaft axis 636. As discussed above with reference to FIGS. 6E and 6F, the transition region 646 of the drive face 642 provides clearance for the driven surfaces 694 when a large offset angle is defined. It should be noted that the drive faces 642 and the driven surfaces 694 do not appear to directly abut one another in the views shown in FIGS. 6G and 6H. In some embodiments, the rounded head 640 and the drive square 690 are sized to provide for a small amount of clearance between the drive faces 642 and the driven surfaces 694 when the rounded head 640 and the drive square 690 are aligned such that the drive faces 642 and the driven surfaces 694 are parallel to one another, as shown in FIGS. 6G and 6H. In some embodiments, such clearance allows for assembly of the reaming device 600 in a manner such that the drive faces 642 and the driven surfaces 694 are not press-fit to one another, and allows space for the adjustment mechanism described herein to operate. In such embodiments, once the drive shaft 630 begins to rotate about the drive axis 636, the drive faces 642 will then pivot accordingly to come into contact with the driven surfaces 694, thereby causing the drive square 690 to rotate.

In some embodiments, the driven surfaces 694 and the drive faces 642 are shaped in a complementary manner to one another also such that, when the drive shaft 630 (including the rounded head 640 and the drive faces 642 thereof) is driven so as to rotate about the drive axis 636, the drive faces 642 apply a torque to the driven surfaces 694 to thereby cause the drive square 690 to rotate about the reaming axis

668. In some embodiments, the drive square 690 includes a groove 698 that is substantially similar to the groove 198 described above.

Continuing to refer to FIGS. 6A-6D, in some embodiments, the reaming device 600 includes a bearing 680 positioned within the bore 666 of the drive square housing 660. In some embodiments, such as shown in FIGS. 6A-6D, the bearing 680 is a plain bearing, such as a bushing. In some embodiments the bearing 180 is a ball bearing or other suitable type of bearing. In some embodiments, the bearing 180 is positioned within the bore 666 of the drive square housing 660 such that, when the orientation of the drive square housing 660 is adjusted as described herein to thereby adjust the orientation of the reaming axis 668, the orientation of the bearing 680 is adjusted correspondingly.

Continuing to refer to FIGS. 6A-6D, in some embodiments, the reaming device 600 includes a housing cap 720. In some embodiments, the housing cap 720 engages the drive square housing 660 (e.g., by threaded engagement as shown in FIG. 6D) to thereby retain the bearing 680 and the drive square 690 within the drive square housing 660.

In some embodiments, use of the reaming device 100 or 600 is performed in accordance with a method that is generally as follows. Use will be described below with specific reference to the reference numbers that correspond to the elements of the reaming device 100, and it should be understood that the reaming device 600 is used in substantially the same manner. In some embodiments, a guide pin (e.g., a Kirschner wire) is fixed to a target area of a patient's glenoid. In some embodiments, the guide pin delineates a neutral axis (e.g., an anatomic axis) of the glenoid. In some embodiments, the reaming head 300 is attached to the reaming device 100 as described above.

In some embodiments, a user (e.g., a surgeon) determines an appropriate offset for the reaming device 100 (e.g., an offset angle between the reaming axis 168 and the drive axis 136 as described above). In some embodiments, the offset is determined based on the condition of the patient's glenoid (e.g., the condition of the bone, the size and shape of a portion or portions of the glenoid that are damaged or diseased, etc.). In some embodiments, the offset is determined based on a selected glenoid implant (e.g., a selected one of the glenoid components of the glenoid component set 510.) In some embodiments, once the offset is selected, a user operates the adjustment knob 230 of the reaming device 100 so as to configure the reaming device 100 to provide the selected offset.

Figures 7A, 7B:
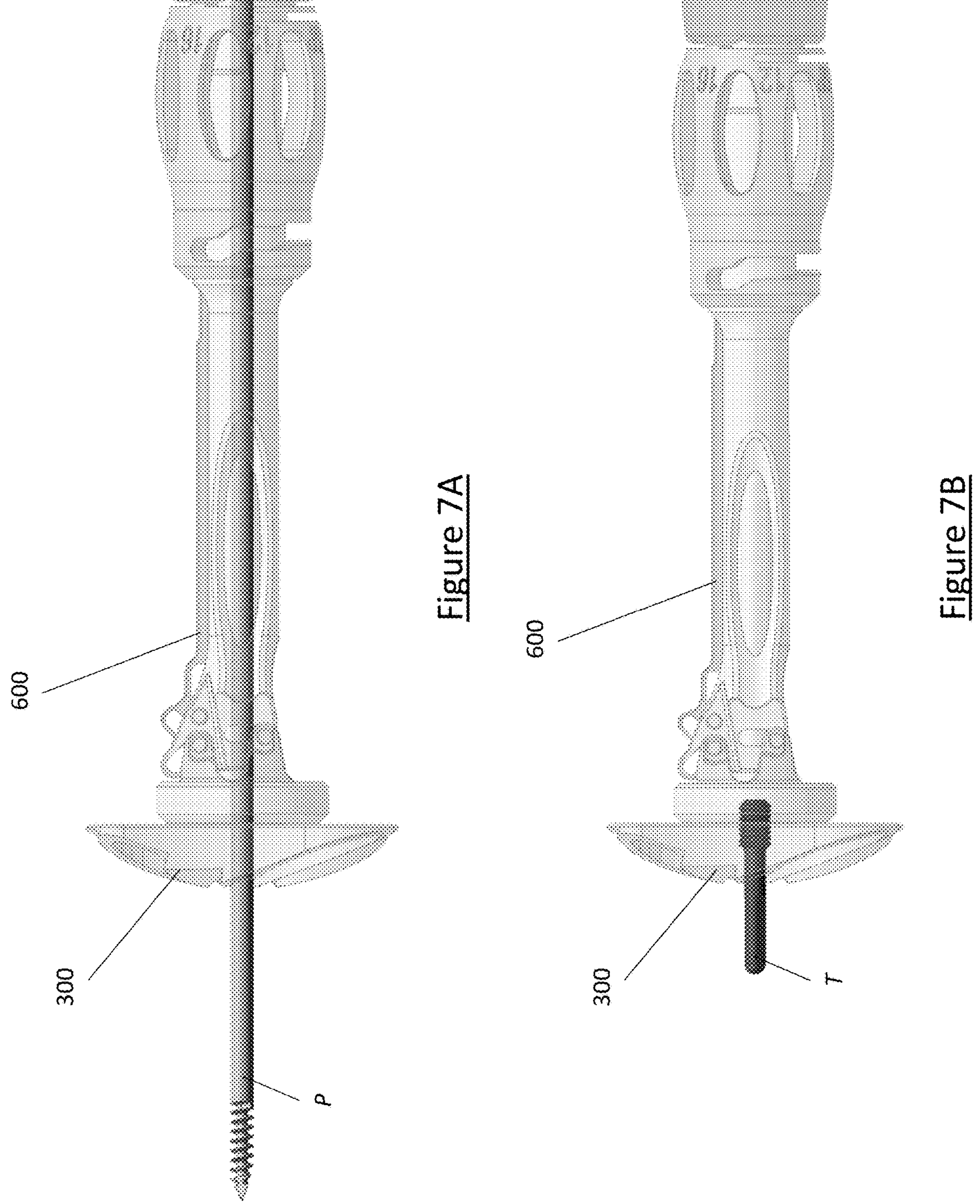
FIG. 7A shows the exemplary reaming device shown in FIG. 3A as assembled with a reaming head and positioned over a representative guide pin indicative of a neutral axis.
FIG. 7B shows the exemplary reaming device shown in FIG. 3A as assembled with a reaming head and a pilot tip.

In some embodiments, a user positions the reaming device 100 over the guide pin such that the guide pin passes through the central bore 306 of the reaming head 300 and into the cannula 138 of the drive shaft 130. FIG. 7A shows the reaming device 600 and the reaming head 300 assembled as described above, and as positioned over a guide pin P. In FIG. 7A, the reaming device 600 and the reaming head 300 are rendered in a transparent manner in order to allow visualization of the guide pin P extending through the reaming device 600 and the reaming head 300. In some embodiments, positioning the guide pin P within the cannula 138 of the drive shaft 130 aligns the drive axis 136 with the neutral axis described above. In some embodiments, a drive mechanism (e.g., a surgical drill or other surgical driver) is coupled to the drive shaft coupling 250 so as to allow the drive mechanism to drive rotation of the drive shaft 130 about the drive axis 136 when the drive mechanism is activated.

In some embodiments, once the guide pin P is positioned within the cannula 138 of the drive shaft 130, a user rotates the reaming device 100 about the guide pin P (and thereby about the drive axis 136) so as to orient the fin 128 toward a defect (e.g., a diseased or damaged region) in the bone to be reamed. As described above, the fin 128 is positioned on the housing 110 in a manner such that the fin 128 is positioned diametrically opposed to the adjustment direction of the reaming device 100. In other words, with reference to FIGS. 4G and 4H, if the drive square housing 160 can be described to pivot about a pivot axis that is transverse to the drive axis 136 when the adjustment knob 230 is actuated to adjust the offset of the reaming axis 168 (e.g., an axis that is parallel to the direction in which the reaming device 100 is viewed in FIGS. 4G and 4H), then the fin 128 extends away from the handle 112 in a direction perpendicular to the pivot axis. Continuing to refer to FIGS. 4G and 4H, when the reaming device 100 is configured so as to provide an offset between the reaming axis 168 and the drive axis 136, and understanding the offset to be in a "downward" direction as shown in FIGS. 4G and 4H, then the portion of the drive square housing 160 (and, thereby, the reaming head 300) that is at the "top" as shown in FIGS. 4G and 4H extends further in a distal direction along the drive axis 136. As such, when the reaming device 100 and the reaming head 300 are operated to ream tissue, the reaming head 300 will extend further (and, thereby, will ream tissue further) at the "top" than at the "bottom". Because the fin 128 is aligned with the "top" direction as described above, aligning the fin with a defect in the bone causes tissue to be reamed to a greater extent in a portion of the bone near the defect and to a lesser extent in a portion of the bone further away from the defect, thereby allowing more healthy bone tissue to be preserved.

It should be noted that the steps described above may be performed in a different order. For example, in some cases, the reaming head 300 may be attached to the reaming device 100 after adjusting the offset of the reaming device 100, the offset of the reaming device 100 may be configured after the reaming device 100 is positioned over the guide pin P, etc.

In some embodiments, once the reaming device 100 has been configured and positioned as described above, a user activates the drive mechanism, thereby activating the reaming device 100 so as to drive the reaming head 300. In some embodiments, a user then advances the reaming device 100 along the guide pin P so as to bring the reaming head 300 into contact with the glenoid of the patient, and continues to advance the reaming device 100 until a desired amount of bone (e.g., an amount sufficient to accommodate a selected one of the glenoid components of the glenoid component set 510) has been reamed from the glenoid. In some embodiments, the user then moves the reaming device 100 away from the glenoid along the guide pin P until disengaged from the guide pin P. Usage of the reaming device 100 is then complete.

In some cases, due to the size of the central bore 306 of the reaming head 300, which is sufficiently large to allow for sufficient offset of the reaming axis 168 as described above, following use of the reaming device 100 a bone shelf may remain around the guide pin P. In some embodiments, a finishing reamer is used to ream the bone shelf to thereby complete preparation of the glenoid to receive a selected glenoid component from the glenoid component set 510. The selected glenoid component may then be secured to the glenoid, and the remainder of the shoulder arthroplasty may then proceed. For example, in cases where a reverse shoulder arthroplasty is being performed, a glenosphere may be secured over the selected glenoid component; in cases where an anatomic shoulder arthroplasty is being performed, the selected glenoid component may itself include a contact surface that contacts a humeral side of the shoulder prosthesis.

Usage of the reaming device 100 is described above with reference to a guide pin (e.g., the guide pin P shown in FIG. 7A) that is fixed in a patient's glenoid prior to application of the reaming device 100 by advancing the cannula 138 of the drive shaft 130 over the guide pin. In other embodiments of a process for usage of the reaming device 100, a guide hole is drilled within the glenoid (e.g., using a surgical drill or other suitable instrument) along the neutral axis rather than fixing a guide pin in the glenoid. In such embodiments, the reaming device 100 includes drive shaft 130 having a cannula 138 that is threaded, and a pilot tip is threaded into the cannula 138. FIG. 7B shows the reaming device 600 as engaged with the reaming head 300 and with a representative pilot tip T threadedly engaged to the reaming device 600. In such embodiments, the pilot tip T is then advanced into the hole that is drilled within the glenoid, thereby aligning the reaming device 100 along the neutral axis in a manner similar to that utilizing a guide pin as described above.

Usage of the reaming device 100 is described above with reference to a guide pin or a guide hole along a neutral axis of a patient's glenoid. In some cases, such as when it is appropriate based on the condition of the given patient's scapula and/or based on a specific glenoid prosthesis to be used, it may be desirable to center the reamed surface elsewhere than along the neutral axis of the glenoid. For such usage techniques, a guide pin or guide hole may be positioned at the desired location and orientation within the glenoid, and usage of the reaming device 100 may then proceed substantially as described above.

In some embodiments, following use of the reaming device 100, disassembly requires only removal of the reaming head 300 from the drive square 190 of the reaming device 100 as described above. In some embodiments, the reaming device 100 is a permanently assembled construct (e.g., none of the elements of the reaming device 100 are disassembled from one another during the typical use cycle) that is composed entirely of parts made from metal and similar heat-tolerant materials. As such, in some embodiments, the reaming device 100 is not disassembled for cleaning and can be sterilized as a whole (e.g., by an autoclave) without requiring any disassembly before cleaning or reassembly after cleaning.

In some embodiments, an advantage provided by the exemplary reaming device 100 described herein is that the reaming device 100 can be utilized to provide a user-configurable offset (e.g., between the reaming axis 168 and the drive axis 136) using only a single guide pin positioned along a neutral axis, such as the guide pin P shown above in FIG. 7A, and without requiring an additional guide pin to be positioned along a reaming axis. In other embodiments, rather than positioning a guide pin within the glenoid, a guide hole is drilled in the glenoid along a neutral axis, and a guide pin is positioned within the cannula 138 of the drive shaft 130 prior to use, and is inserted into the guide hole during use.

In some embodiments, an advantage provided by the exemplary reaming device 100, as provided as part of the kit 500, is that the reaming device 100 provides different offset settings that are indexed to different glenoid components within the glenoid component set 510. Thus, once a clinician has selected a desired one of the glenoid components within the glenoid component set 510 that is suitable for use for a given patient's glenoid, the process of configuring the reaming device 100 to ream the glenoid at a suitable angle requires only operating the adjustment knob 230 to select a one of the indicia 236 that corresponds to the selected one of the glenoid components of the glenoid component set 510, and does not require any further calculations or refinements.

Figure 8:
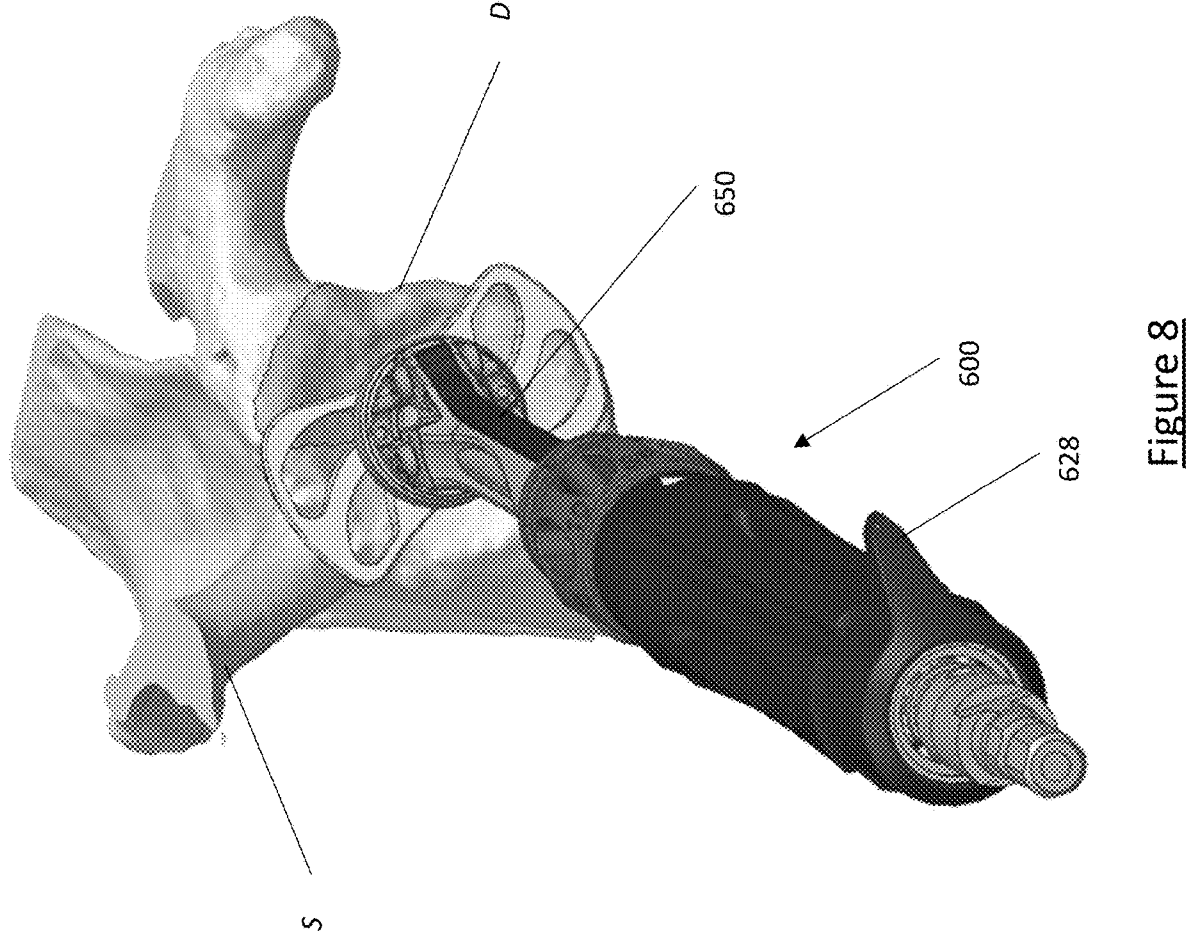
FIG. 8 shows the exemplary reaming device shown in FIG. 6A as assembled with a reaming tip and aligned with respect to a representative defect in a patient's glenoid.

In some embodiments, an advantage provided by the exemplary reaming device 100 or 600 is that the fin 128 or 628 provides a visual cue, at the end of the reaming device 100 or 600 that is held by a user, of the proper orientation of the reaming device 100 or 600 with respect to a defect in a patient's bone. In some embodiments, the linkage 150 or 650 is color-contrasting with respect to the drive shaft sleeve 114 or 614 in order to provide a further such visual cue. By doing so, the exemplary reaming device 100 or 600 enables the user easily to orient the reaming device 100 or 600 so as to align the reaming head 300 with a defect of a patient's glenoid, thereby to minimize the amount of reaming that is required to prepare the bone so as to match a compatible implant. FIG. 8 shows the exemplary reaming device 600 in use to ream tissue from a representative scapula S having a defect D that is rendered in a color-contrasting manner for clarity of illustration. As shown in FIG. 8, the fin 628 and the color-contrasting linkage 650 provide visual confirmation to a user that the reaming device 600 is properly oriented to ream the bone to the greatest depth at the defect D.

In some embodiments, an advantage provided by the exemplary reaming device 100, as assembled with the reaming head 300, is that no direct user interaction with elements of the reaming device 100 that are proximate to the reaming head 300 (e.g., the drive square 190, the bearing 180, the drive square housing 160, etc.) is required to adjust the offset of the reaming axis 168. Rather, adjustment is accomplished by interaction with the adjustment knob 230, which is spaced apart from the reaming head 300 and remains away from the joint space (e.g., outside the body of the patient) when the reaming device 100 is in use. As such, adjustment of the offset of the reaming axis 168 can be made while the reaming device 100 is positioned for use in situ within the body of a patient (e.g., with the cannula 138 of the drive shaft 130 positioned over the guide pin P as shown in FIG. 7A), rather than requiring removal in order to adjust.

The exemplary embodiments described above have been described with specific reference to a reaming device 100 as configured and utilized to treat a glenoid of a patient. In other embodiments, a reaming device may be configured and utilized to treat another bone requiring a reamed surface to be angularly offset from a neutral axis without departing from the broader principles exemplified by the embodiments described above.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:

1. A device for reaming a bone of a patient, comprising:

a housing configured to be gripped by a user, wherein the housing includes a proximal end and a distal end opposite the proximal end, wherein a passage extends through the housing from the proximal end to the distal end, wherein the passage defines a drive shaft axis;

a drive shaft received within the passage, wherein the drive shaft includes a proximal end and a distal end, wherein the drive shaft is supported within the passage so as to be rotatable about the drive shaft axis with respect to the housing, wherein a cannula is formed in the distal end of the drive shaft, wherein the cannula is configured to receive a guide pin;

a drive housing pivotably coupled to the housing, wherein the drive housing defines a reaming axis, wherein the drive housing is pivotable with respect to the housing so as to cause the reaming axis to deflect with respect to the drive shaft axis;

a drive interface element positioned within the drive housing, wherein the drive interface element is supported within the drive housing such that the drive interface element is allowed to rotate about the reaming axis with respect to the drive housing, wherein the drive interface element contacts the distal end of the drive shaft such that rotation of the drive shaft about the drive shaft axis causes rotation of the drive interface element about the reaming axis, wherein the drive interface element is configured to removably receive a reaming head, wherein, when the reaming head is removably received by the drive interface element, rotation of the drive interface element about the reaming axis causes rotation of the reaming head about the reaming axis; and an angle adjustment control element positioned remotely from the distal end of the housing, wherein the angle adjustment control element is operably coupled to the drive housing, wherein the angle adjustment control element is operable to move the drive housing between at least:

a first position, wherein the drive housing defines a first offset angle between the reaming axis and the drive shaft axis, and a second position, wherein the drive housing defines a second offset angle between the reaming axis and the drive shaft axis, wherein the second offset angle is greater than the first offset angle.

2. The device of claim 1, wherein the distal end of the drive shaft includes at least one torque transmitting surface, wherein the drive interface element includes at least one torque receiving surface, and wherein the drive interface element is positioned within the drive housing such that the at least one torque transmitting surface of the drive shaft and the at least one torque receiving surface of the drive interface element abut one another.

3. The device of claim 1, further comprising:

a linkage coupling the angle adjustment control element to the drive housing.

4. The device of claim 3, wherein the linkage has a proximal end and a distal end opposite the proximal end of the linkage, wherein the angle adjustment control element is positioned on the housing so as to be pivotable with respect to the housing about the drive shaft axis, wherein the linkage is positioned on the housing so as to be movable with respect to the housing along the drive shaft axis, wherein the angle adjustment control element engages the proximal end of the linkage such that pivoting movement of the angle adjustment control element about the drive shaft axis causes linear movement of the linkage along the drive shaft axis, and wherein the distal end of the linkage engages the drive housing such that linear movement of the linkage along the drive shaft axis causes the drive housing to pivot so as to adjust the offset angle.

5. The device of claim 3, wherein the linkage is color-contrasting so as to identify a proper orientation of the device about a guide pin.

6. The device of claim 1, wherein the housing comprises a fin, wherein the fin extends from the proximal end of the housing, and wherein the fin is positioned so as to identify a proper orientation of the device about a guide pin.

7. The device of claim 1, further comprising:

a reaming head removably engaged to the drive interface element.

8. The device of claim 7, wherein the drive interface element comprises a plurality of torque transmitting surfaces, wherein the reaming head comprises a plurality of torque receiving surfaces, and wherein each of the plurality of torque transmitting surfaces of the drive interface element abuts a corresponding one of the plurality of torque receiving surfaces of the reaming head when the reaming head is removably engaged to the drive interface element, whereby the drive interface element drives rotation of the reaming head about the reaming axis when the drive interface element is rotated about the reaming axis.

9. The device of claim 7, wherein the reaming head comprises a central bore, wherein the central bore is sized to allow the guide pin to pass through the central bore and into the cannula of the drive shaft.

10. The device of claim 1, wherein the angle adjustment control element is configured to allow a user to adjust the offset angle without the user contacting a distal end of the device.

11. The device of claim 1, wherein the angle adjustment control element comprises an adjustment knob.

12. The device of claim 11, wherein the adjustment knob is positioned on the housing between the proximal end of the housing and the distal end of the housing.

13. A kit, comprising:

the device of claim 1;

a reaming head configured to removably engage the drive interface element of the device;

a first glenoid component of a shoulder prosthesis, wherein the first glenoid component comprises a first augment angle, and wherein the first augment angle corresponds to the first offset angle between the reaming axis and the drive axis; and a second glenoid component of a shoulder prosthesis, wherein the second glenoid component comprises a second augment angle, and wherein the second augment angle corresponds to the second offset angle between the reaming axis and the drive axis.

14. A method, comprising:

positioning one of a guide pin or a guide hole along a neutral axis of a glenoid of a of a patient;

providing a surgical reamer driver, wherein the surgical reamer driver comprises:

a housing configured to be gripped by a user, wherein the housing includes a proximal end and a distal end opposite the proximal end, wherein a passage extends through the housing from the proximal end to the distal end, wherein the passage defines a drive shaft axis;

a drive shaft received within the passage, wherein the drive shaft includes a proximal end and a distal end, wherein the drive shaft is supported within the passage so as to be rotatable about the drive shaft axis with respect to the housing, wherein a cannula is formed in the distal end of the drive shaft, wherein the cannula is configured to receive a guide pin;

a drive housing pivotably coupled to the housing, wherein the drive housing defines a reaming axis, wherein the drive housing is pivotable with respect to the housing so as to cause the reaming axis to deflect with respect to the drive shaft axis;

a drive interface element positioned within the drive housing, wherein the drive interface element is supported within the drive housing such that the drive interface element is allowed to rotate about the reaming axis with respect to the drive housing, wherein the drive interface element contacts the distal end of the drive shaft such that rotation of the drive shaft about the drive shaft axis causes rotation of the drive interface element about the reaming axis, wherein the drive interface element is configured to removably receive a reaming head, wherein, when the reaming head is removably received by the drive interface element, rotation of the drive interface element about the reaming axis causes rotation of the reaming head about the reaming axis; and an angle adjustment control element positioned remotely from the distal end of the housing, wherein the angle adjustment control element is operably coupled to the drive housing, wherein the angle adjustment control element is operable to move the drive housing between at least:

a first position, wherein the drive housing defines a first offset angle between the reaming axis and the drive shaft axis, and a second position, wherein the drive housing defines a second offset angle between the reaming axis and the drive shaft axis, wherein the second offset angle is greater than the first offset angle;

configuring the surgical reamer driver to provide a selected one of the first offset angle or the second offset angle;

coupling a reaming head to the surgical reamer driver;

advancing the cannula of the drive shaft of the surgical reamer driver along the one of the guide pin or the guide hole; and operating the surgical reamer driver to ream bone of the glenoid, glenoid component on the glenoid.

15. The method of claim 14, further comprising:

prior to operating the surgical reamer driver to ream the bone of the glenoid, aligning the surgical reamer driver about the guide pin with reference to a defect in the glenoid.

16. The method of claim 15, wherein the aligning is performed by aligning a visual indicator of the surgical reamer driver with the defect.

17. The method of claim 16, wherein the visual indicator comprises at least one of a protrusion from the surgical reamer driver or a color-contrasting element of the surgical reamer driver.

18. The method of claim 14, further comprising:

selecting a selected glenoid component of a shoulder prosthesis from a set of glenoid components.

19. The method of claim 18, wherein the selected glenoid component comprises a selected augment angle, and wherein the selected augment angle corresponds to the selected one of the first offset angle or the second offset angle.

20. The method of claim 19, further comprising:

after operating the surgical reamer drive to ream the bone of the glenoid, implanting the selected glenoid component on the glenoid.

21. The method of claim 14, wherein the positioning one of the guide pin or the guide hole along a neutral axis of a glenoid of a of a patient comprises forming the guide hole in the glenoid, and wherein the advancing the cannula of the drive shaft of the surgical reamer driver along the guide hole comprises: placing a pilot tip in the cannula of the drive shaft, and advancing the pilot tip into the guide hole.

* * * * *